(12) United States Patent
Bosio

(10) Patent No.: US 9,133,263 B2
(45) Date of Patent: Sep. 15, 2015

(54) METHOD FOR THE SEPARATION OF CELLS

(75) Inventor: Andreas Bosio, Cologne (DE)

(73) Assignee: MILTENYI BIOTEC GMBH, Bergisch Gladbach (DE)

( * ) Notice: Subject to any disclaimer, the term of this patent is extended or adjusted under 35 U.S.C. 154(b) by 721 days.

(21) Appl. No.: 12/743,395

(22) PCT Filed: Nov. 20, 2008

(86) PCT No.: PCT/IB2008/003708
§ 371 (c)(1),
(2), (4) Date: Aug. 10, 2010

(87) PCT Pub. No.: WO2009/066180
PCT Pub. Date: May 28, 2009

(65) Prior Publication Data
US 2011/0004952 A1    Jan. 6, 2011

(30) Foreign Application Priority Data
Nov. 20, 2007   (EP) .................................... 07022478

(51) Int. Cl.
*A01K 67/00* (2006.01)
*C12N 15/00* (2006.01)
*C07K 14/705* (2006.01)
*C12N 5/0735* (2010.01)
*C12N 5/00* (2006.01)

(52) U.S. Cl.
CPC ......... *C07K 14/705* (2013.01); *C07K 14/70589* (2013.01); *C07K 14/70596* (2013.01); *C12N 5/0606* (2013.01); *C12N 2510/00* (2013.01)

(58) Field of Classification Search
CPC .................. C07K 14/70596; C07K 14/70589; C07K 14/705; C12N 5/0606
USPC .............................................. 800/8; 435/325
See application file for complete search history.

(56) References Cited

PUBLICATIONS

Mazumdar et al Sep. 2007, Genesis 45:593-605.*
Awatramani et al 2001, Nature Genetics 29:257-259.*
Banares et al., Genesis, 42:6-16 (2005). "Novel pan-neuronal Cre-transgenic line for conditional ablation of genes in the nervous system."
Breitman et al., Reports, 1563-1565 (1987). "Genetic ablation: targeted expression of a toxin gene causes microphthalmia in transgenic mice."
Buch et al., Nature Methods, 2(6):419-426 (2005). "A Cre-inducible diphtheria toxin receptor mediates cell lineage ablation after toxin administration."
Gaines and Wojchowski, BioTechniques, 26(4):683-688 (1999). "pIRES-CD4t, a dicistronic expression vector for MACS- or FACS-based selection of transfected cells."
Kantor et al., Cell Separation Methods and Applications (Recktenwald Radbruch), Chapter 8, pp. 153-173 (1998). "Magnetic cell sorting with colloidal superparamagnetic particles."
Lakso et al., Proc. natl. Acad. Sci. USA, 89:6232-6236 (1992). "Targeted oncogene activation by site-specific recombination in transgenic mice."
Lucast et al., BioTechniques, 30:544-554 (2001). "Large-scale purification of a stable form of recombinant tobacco etch virus protease."
Palmiter et al., Cell, 50:435-443 (1987). "Cell lineage ablation in transgenic mice by cell-specific expression of a toxin gene."
Seidenfaden et al., Mol. Cell. Neurosci., 32: 187-198 (2006). "Glial conversion of SVZ-derived committed neuronal precursors after ectopic grafting into the adult brain."
Suzuki et al., Neuroscience Research, 47:451-454 (2003). "A transgenic mouse model for the detailed morphological study of astrocytes."
Yasunaga et al., Nature Biotechnology, 23(12):1542-1550 (2005). "Induction and monitoring of definitive and visceral endoderm differentiation of mouse ES cells."
Zambrowicz et al., PNAS, 94:3789-3794 (1997). "Disruption of overlapping transcripts in the ROSA beta geo 26 gene trap strain leads to widespread expression of beta-galactosidase in mouse embryos and hematopoietic cells."
Berghuis, P. et al., International Journal of Developmental Neuroscience, 22(7):533-543 (2004). "Turning the heterogeneous into homogeneous: studies on selectively isolated GABAergic interneuron subsets."
David, R. et al., Stem Cells, 23(4):477-482 (2005). "Magnetic cell sorting purification of differentiated embryonic stem cells stably expressing truncated human CD4 as surface marker."
Kondoh, G. et al., FEBS Letters, 458 (3):299-303 (1999). "Tissue-inherent fate of GPI revealed by GPI-anchored GFP transgenesis."
Le, Y. et al., Methods in Molecular Biology, 136(3); 477-485 (2000). "Conditional gene knockout using CRE recombinase."
Liu, G. et al., Molecular Cancer, 5(1):67 (2006). "Analysis of gene expression and chemoresistance of CD133+ cancer stem cells in glioblastoma."
Rhee, J.M. et al., Genesis the Journal of Genetics and Development, 44(4):202-218 (2006). "In vivo imaging and differential localization of lipid-modified GFP-variant fusions in embryonic stem cells and mice."
Schindehutte, J. et al., Stem Cells, Alphamed Press, 23(1):10-15 (2005). "In vivo and in vitro tissue-specific expression of green fluorescent protein using the cre-lox system in mouse embryonic stem cells."

* cited by examiner

*Primary Examiner* — Christopher M Babic
*Assistant Examiner* — Kelaginamane T Hiriyanna
(74) *Attorney, Agent, or Firm* — Nixon Peabody LLP; Mark J. FitzGerald

(57) ABSTRACT

The invention relates to a cell containing a gene encoding a conditional transgenic surface marker that is detectable upon expression on the surface of the cell, wherein the gene encoding a conditional transgenic surface marker comprises: (i) a promoter, operably linked to (ii) a first transcription sequence, and (iii) a second transcription sequence encoding the surface marker, whereby the first transcription sequence prevents the transcription of the second transcription sequence, whereby the first transcription sequence is conditionally removable such that the second transcription sequence is transcribable, and whereby the surface marker renders the cell sortable through the detection of the conditional transgenic surface marker. Furthermore, the invention relates to a construct for generating such a cell, and to a method for separating such a cell from a population of cells.

7 Claims, 9 Drawing Sheets

H2Kk- iSE-H2Kk-ES cells
2 days after MACS

H2Kk+ iSE-H2Kk-ES cells
2 days after MACS

SEQUENCE LISTING

```
<160> NUMBER OF SEQ ID NOS: 9

<210> SEQ ID NO 1
<211> LENGTH: 865
<212> TYPE: PRT
<213> ORGANISM: Homo sapiens

<400> SEQUENCE: 1

Met Ala Leu Val Leu Gly Ser Leu Leu Leu Leu Gly Leu Cys Gly Asn
1               5                   10                  15

Ser Phe Ser Gly Gly Gln Pro Ser Ser Thr Asp Ala Pro Lys Ala Trp
                20                  25                  30

Asn Tyr Glu Leu Pro Ala Thr Asn Tyr Glu Thr Gln Asp Ser His Lys
            35                  40                  45

Ala Gly Pro Ile Gly Ile Leu Phe Glu Leu Val His Ile Phe Leu Tyr
        50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95
```

-continued

```
Ile Leu Gly Leu Lys Ile Val Tyr Tyr Glu Ala Gly Ile Ile Leu Cys
            100                 105                 110
Cys Val Leu Gly Leu Leu Phe Ile Ile Leu Met Pro Leu Val Gly Tyr
            115                 120                 125
Phe Phe Cys Met Cys Arg Cys Cys Asn Lys Cys Gly Gly Glu Met His
130                 135                 140
Gln Arg Gln Lys Glu Asn Gly Pro Phe Leu Arg Lys Cys Phe Ala Ile
145                 150                 155                 160
Ser Leu Leu Val Ile Cys Ile Ile Ser Ile Gly Ile Phe Tyr Gly
                165                 170                 175
Phe Val Ala Asn His Gln Val Arg Thr Arg Ile Lys Arg Ser Arg Lys
            180                 185                 190
Leu Ala Asp Ser Asn Phe Lys Asp Leu Arg Thr Leu Leu Asn Glu Thr
            195                 200                 205
Pro Glu Gln Ile Lys Tyr Ile Leu Ala Gln Tyr Asn Thr Thr Lys Asp
            210                 215                 220
Lys Ala Phe Thr Asp Leu Asn Ser Ile Asn Ser Val Leu Gly Gly Gly
225                 230                 235                 240
Ile Leu Asp Arg Leu Arg Pro Asn Ile Ile Pro Val Leu Asp Glu Ile
                245                 250                 255
Lys Ser Met Ala Thr Ala Ile Lys Glu Thr Lys Glu Ala Leu Glu Asn
                260                 265                 270
Met Asn Ser Thr Leu Lys Ser Leu His Gln Gln Ser Thr Gln Leu Ser
            275                 280                 285
Ser Ser Leu Thr Ser Val Lys Thr Ser Leu Arg Ser Ser Leu Asn Asp
            290                 295                 300
Pro Leu Cys Leu Val His Pro Ser Ser Glu Thr Cys Asn Ser Ile Arg
305                 310                 315                 320
Leu Ser Leu Ser Gln Leu Asn Ser Asn Pro Glu Leu Arg Gln Leu Pro
                325                 330                 335
Pro Val Asp Ala Glu Leu Asp Asn Val Asn Asn Val Leu Arg Thr Asp
            340                 345                 350
Leu Asp Gly Leu Val Gln Gln Gly Tyr Gln Ser Leu Asn Asp Ile Pro
            355                 360                 365
Asp Arg Val Gln Arg Gln Thr Thr Thr Val Val Ala Gly Ile Lys Arg
370                 375                 380
Val Leu Asn Ser Ile Gly Ser Asp Ile Asp Asn Val Thr Gln Arg Leu
385                 390                 395                 400
Pro Ile Gln Asp Ile Leu Ser Ala Phe Ser Val Tyr Val Asn Asn Thr
                405                 410                 415
Glu Ser Tyr Ile His Arg Asn Leu Pro Thr Leu Glu Glu Tyr Asp Ser
                420                 425                 430
Tyr Trp Trp Leu Gly Gly Leu Val Ile Cys Ser Leu Leu Thr Leu Ile
            435                 440                 445
Val Ile Phe Tyr Tyr Leu Gly Leu Leu Cys Gly Val Cys Gly Tyr Asp
        450                 455                 460
Arg His Ala Thr Pro Thr Thr Arg Gly Cys Val Ser Asn Thr Gly Gly
465                 470                 475                 480
Val Phe Leu Met Val Gly Val Gly Leu Ser Phe Leu Phe Cys Trp Ile
            485                 490                 495
Leu Met Ile Ile Val Val Leu Thr Phe Val Phe Gly Ala Asn Val Glu
            500                 505                 510
```

Lys Leu Ile Cys Glu Pro Tyr Thr Ser Lys Glu Leu Phe Arg Val Leu
            515                 520                 525

Asp Thr Pro Tyr Leu Leu Asn Glu Asp Trp Glu Tyr Tyr Leu Ser Gly
        530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
        595                 600                 605

Leu Leu Gly Ala Ala Gly Arg Lys Asn Leu Gln Asp Phe Ala Ala Cys
    610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Gly Arg Val Leu Pro Ile
        675                 680                 685

Glu Gln Ser Leu Ser Thr Leu Tyr Gln Ser Val Lys Ile Leu Gln Arg
    690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
                725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
        755                 760                 765

Lys Pro Val Ala Thr Ala Leu Asp Thr Ala Val Asp Val Phe Leu Cys
    770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
            820                 825                 830

Thr Ile Pro Met Lys Asn Met Glu Asn Gly Asn Asn Gly Tyr His Lys
        835                 840                 845

Asp His Val Tyr Gly Ile His Asn Pro Val Met Thr Ser Pro Ser Gln
    850                 855                 860

His
865

<210> SEQ ID NO 2
<211> LENGTH: 256
<212> TYPE: PRT
<213> ORGANISM: Homo sapiens

```
<400> SEQUENCE: 2

Asn His Gln Val Arg Thr Arg Ile Lys Arg Ser Arg Lys Leu Ala Asp
1               5                   10                  15

Ser Asn Phe Lys Asp Leu Arg Thr Leu Leu Asn Glu Thr Pro Glu Gln
            20                  25                  30

Ile Lys Tyr Ile Leu Ala Gln Tyr Asn Thr Thr Lys Asp Lys Ala Phe
        35                  40                  45

Thr Asp Leu Asn Ser Ile Asn Ser Val Leu Gly Gly Gly Ile Leu Asp
    50                  55                  60

Arg Leu Arg Pro Asn Ile Ile Pro Val Leu Asp Glu Ile Lys Ser Met
65                  70                  75                  80

Ala Thr Ala Ile Lys Glu Thr Lys Glu Ala Leu Glu Asn Met Asn Ser
                85                  90                  95

Thr Leu Lys Ser Leu His Gln Gln Ser Thr Gln Leu Ser Ser Ser Leu
            100                 105                 110

Thr Ser Val Lys Thr Ser Leu Arg Ser Ser Leu Asn Asp Pro Leu Cys
        115                 120                 125

Leu Val His Pro Ser Ser Glu Thr Cys Asn Ser Ile Arg Leu Ser Leu
    130                 135                 140

Ser Gln Leu Asn Ser Asn Pro Glu Leu Arg Gln Leu Pro Pro Val Asp
145                 150                 155                 160

Ala Glu Leu Asp Asn Val Asn Asn Val Leu Arg Thr Asp Leu Asp Gly
                165                 170                 175

Leu Val Gln Gln Gly Tyr Gln Ser Leu Asn Asp Ile Pro Asp Arg Val
            180                 185                 190

Gln Arg Gln Thr Thr Thr Val Val Ala Gly Ile Lys Arg Val Leu Asn
        195                 200                 205

Ser Ile Gly Ser Asp Ile Asp Asn Val Thr Gln Arg Leu Pro Ile Gln
    210                 215                 220

Asp Ile Leu Ser Ala Phe Ser Val Tyr Val Asn Asn Thr Glu Ser Tyr
225                 230                 235                 240

Ile His Arg Asn Leu Pro Thr Leu Glu Glu Tyr Asp Ser Tyr Trp Trp
                245                 250                 255

<210> SEQ ID NO 3
<211> LENGTH: 289
<212> TYPE: PRT
<213> ORGANISM: Homo sapiens

<400> SEQUENCE: 3

Thr Phe Val Phe Gly Ala Asn Val Glu Lys Leu Ile Cys Glu Pro Tyr
1               5                   10                  15

Thr Ser Lys Glu Leu Phe Arg Val Leu Asp Thr Pro Tyr Leu Leu Asn
            20                  25                  30

Glu Asp Trp Glu Tyr Tyr Leu Ser Gly Lys Leu Phe Asn Lys Ser Lys
        35                  40                  45

Met Lys Leu Thr Phe Glu Gln Val Tyr Ser Asp Cys Lys Lys Asn Arg
    50                  55                  60

Gly Thr Tyr Gly Thr Leu His Leu Gln Asn Ser Phe Asn Ile Ser Glu
65                  70                  75                  80

His Leu Asn Ile Asn Glu His Thr Gly Ser Ile Ser Ser Glu Leu Glu
                85                  90                  95

Ser Leu Lys Val Asn Leu Asn Ile Phe Leu Leu Gly Ala Ala Gly Arg
            100                 105                 110
```

```
Lys Asn Leu Gln Asp Phe Ala Ala Cys Gly Ile Asp Arg Met Asn Tyr
            115                 120                 125

Asp Ser Tyr Leu Ala Gln Thr Gly Lys Ser Pro Ala Gly Val Asn Leu
    130                 135                 140

Leu Ser Phe Ala Tyr Asp Leu Glu Ala Lys Ala Asn Ser Leu Pro Pro
145                 150                 155                 160

Gly Asn Leu Arg Asn Ser Leu Lys Arg Asp Ala Gln Thr Ile Lys Thr
                165                 170                 175

Ile His Gln Gln Arg Val Leu Pro Ile Glu Gln Ser Leu Ser Thr Leu
            180                 185                 190

Tyr Gln Ser Val Lys Ile Leu Gln Arg Thr Gly Asn Gly Leu Leu Glu
    195                 200                 205

Arg Val Thr Arg Ile Leu Ala Ser Leu Asp Phe Ala Gln Asn Phe Ile
210                 215                 220

Thr Asn Asn Thr Ser Ser Val Ile Ile Glu Glu Thr Lys Lys Tyr Gly
225                 230                 235                 240

Arg Thr Ile Ile Gly Tyr Phe Glu His Tyr Leu Gln Trp Ile Glu Phe
                245                 250                 255

Ser Ile Ser Glu Lys Val Ala Ser Cys Lys Pro Val Ala Thr Ala Leu
            260                 265                 270

Asp Thr Ala Val Asp Val Phe Leu Cys Ser Tyr Ile Ile Asp Pro Leu
    275                 280                 285

Asn

<210> SEQ ID NO 4
<211> LENGTH: 8
<212> TYPE: PRT
<213> ORGANISM: Artificial
<220> FEATURE:
<223> OTHER INFORMATION: TAG2, no homology to any existing mammalian
      sequence

<400> SEQUENCE: 4

Asn Glu Gly Val Tyr Ser Asp Gln
1               5

<210> SEQ ID NO 5
<211> LENGTH: 8
<212> TYPE: PRT
<213> ORGANISM: Artificial
<220> FEATURE:
<223> OTHER INFORMATION: TAG2, no homology to any existing mammalian
      sequence

<400> SEQUENCE: 5

Asp Gln Asn Ser Gln Asp Glu Glu
1               5

<210> SEQ ID NO 6
<211> LENGTH: 8
<212> TYPE: PRT
<213> ORGANISM: Artificial
<220> FEATURE:
<223> OTHER INFORMATION: TAG2, no homology to any existing mammalian
      sequence

<400> SEQUENCE: 6

Ser Asp Asp Glu Asp Gln Glu Gln
1               5
```

```
<210> SEQ ID NO 7
<211> LENGTH: 8
<212> TYPE: PRT
<213> ORGANISM: Artificial
<220> FEATURE:
<223> OTHER INFORMATION: TAG2, no homology to any existing mammalian
      sequence

<400> SEQUENCE: 7

Asp Glu Tyr Asp His Tyr Val Asp
1               5

<210> SEQ ID NO 8
<211> LENGTH: 9
<212> TYPE: PRT
<213> ORGANISM: Artificial
<220> FEATURE:
<223> OTHER INFORMATION: TAG2, no homology to any existing mammalian
      sequence

<400> SEQUENCE: 8

Asp Phe Lys Asp Glu Asp Phe Lys Asp
1               5

<210> SEQ ID NO 9
<211> LENGTH: 7
<212> TYPE: PRT
<213> ORGANISM: Artificial
<220> FEATURE:
<223> OTHER INFORMATION: Protease recognition sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Ser can alternatively be Gly

<400> SEQUENCE: 9

Glu Xaa Xaa Tyr Xaa Gln Ser
1               5
```

METHOD FOR THE SEPARATION OF CELLS

CROSS-REFERENCE TO RELATED APPLICATIONS

This application is a 35 U.S.C. §371 National Stage of International Application No. PCT/IB2008/003708 filed on Nov. 20, 2008, which designates the United States, and which claims the benefit of priority under 35 U.S.C. §119(a) of European Application No. 07022478.7 filed on Nov. 30, 2007, the contents of which are incorporated herein by reference.

The invention relates to a cell containing a gene encoding a conditional transgenic surface marker that is detectable upon expression of the marker on the surface of the cell. Furthermore, the invention relates to a construct for generating such a cell, and to a method for separating such a cell from a population of cells.

BACKGROUND OF THE INVENTION

Separation and isolation of specific cell types in the context of whole organisms allows their separated cultivation and functional as well as molecular analysis. This has turned out to be very useful for the understanding of specific cell populations and their interaction with other cells but also for their manipulation and therapeutic use.

Numerous methods have been formulated to analyze and sort populations of cells including, but not limited to methods using the size, density or granularity of a cell for a separation by sedimentation which can be performed on its own or in combination with density gradients and centrifugation or elutriation. Further methods are based on the different resistance of cells to osmotic lysis for the separation of e.g. white blood cells from blood. Furthermore, methods of depletion of unwanted cells using specific toxic antibodies reacting with a cell surface marker can be used. Further methods are for example flow cytometry or magnetic cell sorting (e.g. using magnetic bead-conjugated antibodies, e.g. MACS, Miltenyi Biotec) and other methods reliant upon antibody affinity to particular surface molecules like proteins. Using the latter technologies, positive enrichment or depletion of cells can be achieved expressing a certain molecule including but not limited to RNA, DNA, lipid, sugar or protein.

It has been reported that a recombinantly expressed green fluorescent protein (GFP) could be located to the cytosolic face of the plasma membrane of mouse embryonic stem cells due to a palmitoylation site that was present in the recombinant GFP. It was speculated that cells expressing such GFP proteins could be separated from cells not expressing this recombinant GFP using fluorescence activated cell sorting (FACS) (Schindehütte et al. (2005) Stem Cells 23:10-15).

In both flow cytometry and magnetic cell sorting, the protein marker is labeled via a specific antibody which again is directly or indirectly coupled to a fluorescent dye or a superparamagnetic particle (bead). Both, intracellular as well as extracellular markers may be used. However, when living cells need to be obtained, so far only extracellular markers could be used as the cell has to be fixed and permeabilized for intracellular staining.

Therefore, so far only those non transgenic cell types were accessible to magnetic cell sorting and flow cytometry of living cells in the context of a whole organism where surface markers were known and specific, high affinity antibodies were available (Recktenwald and Radbruch, Cell Separation Methods and Applications (1998), 153-174).

As mentioned, many additional cell types are characterized by intracellular markers like cytoskeletal proteins, transcription factors, specific organelle proteins, enzymes, etc. (Berghuis et al. (2004) Int J Dev Neurosci 22:533-43).

Among others, these intracellular markers have been used to generate mouse lines expressing a cell type specific reporter by using the respective promoter (Suzuki et al. (2003) Neurosci Res 47:451-454; Lakso et al. (1992) Proc Natl Acad Sci USA 89: 6232-6236; Zambrowicz et al. (1997) Proc Natl Acad Sci USA 94:3789-94; David et al. (2005) Stem Cells 23:477-482).

Furthermore, certain cell types are characterized in addition or only by spatio-temporal parameters. That means that these cells are not, or not only characterized by the expression of a marker but by their limited occurrence within a certain region or part of an organ or organism and/or by their limited occurrence within a certain time period. For example, cells present only in the amygdalla of the brain, cells having a certain function only during the early postnatal period, cells having certain functions after a lesion of an organ, or cells changing their behavior after a drug treatment.

However, the reporter used in combination with intracellular markers or spatio-temporal properties so far are either fluorescent reporters (like green fluorescent protein (GFP), yellow fluorescent protein (YFP), etc.) or other reporters which can be used to stain a cell (e.g. beta galactosidase). In some cases, transgenes have been introduced which allow for a depletion of a specific cell line by expressing the diphtheria toxin receptor (DTR) (Buch et al. (2005) Nature Methods 2:419-426) or directly the diphtheria toxin A subunit (DT-A) (Palmiter et al. (1987) Cell 50:435-443; Breitmann et al. (1987) Science 238:1563-1565).

Lastly, it has also been reported that under certain conditions and for some markers it may be possible to partially degrade the surface of a cell to access intracellular markers but still keeping a cell alive (Berghuis et al. (2004) Int J Dev Neurosci 22:533-43).

In case of flow sorting, fluorescent reporters can be used for the isolation of living cells. Although high speed flow cytometry sorting instruments have been developed which allow the separation of several ten thousand cells per second, it would be a great step forward if sorting techniques like magnetic cell sorting could be used for the isolation of cells or biological entities derived thereof, characterized by an intracellular marker or spatio-temporal properties. Immunomagnetic cell sorting, e.g. MACS Cell Separation System, allows to separate several billion cells in a few minutes, is much less cumbersome and much more cost effective than flow cytometry, as no complex instrument nor a highly skilled operator are needed.

For cell lines and primary cells which are cultivated ex vivo, several methods have been reported for introduction of a transgenic cell surface marker in order to subsequently make these cells sortable using flow cytometry or magnetic cell sorting (Gaines et al. (1999) Biotechniques 26:683-688). In brief, cells are transfected with a construct leading to the expression of a surface marker which again can be addressed by a specific antibody carrying a fluorescent tag or a superparamagnetic bead. This approach can also be extended to the expression of a transgenic cell surface marker in cells of a whole organism using appropriate transfection methods like viral vectors, pronucleus injection, or gene targeting approaches (Yasunaga et al. (2005) Nat Biotech 23: 1542-1550).

It is, however, not predictable for a person of skill in the art whether a transgenic or transfected whole organism is going to express a reporter as wanted. Exogenous transgenes may not harbor all of the sequences necessary and sufficient for proper regulation of transcription and may therefore be influenced by e.g. cis-regulatory elements near the site of insertion (Banares et al. (2005) Genesis 42:6-16). Therefore, the generation and characterization e.g. of proper transgenic mice is still cumbersome and time consuming.

As for the nature of transgenic surface markers, several different possibilities haven been mentioned in the literature (see above, e.g. CD4, LNGFR, H2Kk, DTR). Most of these markers are naturally occurring proteins which are ectopically expressed to indicate the transgenic status of a cell. Some of these proteins like CD4 and LNGFR have in addition been engineered to have a deleted or mutated intracellular domain in order to avoid signaling upon antibody binding of the extracellular domain. However, none of the proteins mentioned in the literature is adequate to be used in all cell sorting and downstream experiments covering different tissue sources, cell types, and protocols for the application of sorted or sorting cells. Some of these proteins like CD4 are not trypsin or papain resistant and thus cannot be used in protocols in which cells are singularized from solid tissues prior sorting. Some other proteins are multiple transmembrane proteins and are therefore partly not expressed appropriately as a transgene. Also, proteins may be toxic or have at least an unwanted impact on their neighboring cells when expressed ectopically on the cell surface of at least some cell types. Lastly, some proteins, like DTR, are internalized upon antibody reaction.

Furthermore, once cells have been isolated, they are often functionally characterized by grafting them into recipient organisms. For example, the neurogenic potential of neural precursors is assessed by placing them into different brain areas (Seidenpfaden et al. (2006) Mol. Cell. Neurosci. 32:187). Comparably, approaches towards regenerative medicine aim to test different cell types and aggregates derived thereof for their repopulating capacity in model organisms or patients. The rejection of donor cells can in general be avoided by performing autologous transplantations or by using inbred strains in case of preclinical research. But conventional transgenic surface epitopes most probably will trigger an immune response and eventually the rejection of the cells if the recipient is not immune suppressed or the transgenic epitope is not identical to an endogenously expressed epitope. The latter would prohibit distinguishing the grafted cells from the host cells by the transgenic surface epitope after grafting. As will be explained below, this is surprisingly achieved by means of the present invention.

DESCRIPTION OF THE INVENTION

Accordingly, the problem underlying the present invention was to provide means for the separation of a particular living cell from a population of living cells, whereby an intracellular cell marker could also be used.

This problem is solved by providing a gene and a cell containing such a gene encoding a conditional transgenic surface marker that is detectable upon expression on the surface of the cell without the need to rupture the cell membrane or destroy the integrity of the cell. The gene encoding a conditional transgenic surface marker comprises:
(i) a promoter, operably linked to
(ii) a first transcription sequence, also referred to as STOP DNA herein, and
(iii) a second transcription sequence encoding the surface marker (reporter),
whereby the first transcription sequence (the STOP DNA) prevents the transcription of the second transcription sequence, and also is conditionally removable such that the second transcription sequence can be transcribed to yield a transgenic cell expressing the conditional transgenic surface marker. In addition, the surface marker is of a kind that renders the cell sortable through the detection of this surface marker.

The second transcription sequence encoding the surface marker, comprises
(a) optionally, a first tag sequence for specifically binding to an antibody positioning at the cytosolic face of the plasma membrane of a cell, or
(b) a transmembrane or membrane association domain for positioning or anchoring the surface marker in the cell membrane, such that the surface marker can be detected from the extracellular side; and
(c) a second tag sequence for rendering a cell sortable, in particular by specifically binding on the extracellular side of a cell to an antibody.

The first tag sequence or the transmembrane or membrane association domain can in one embodiment at least partially overlap with the second tag sequence.

Since the cell surface marker is a protein with at least one transmembrane and/or membrane association domain (like a GPI anchor) it is therefore being positioned at the cell membrane such that at least a portion of the protein is on the extracellular part of the cell, rendering it detectable with e.g. an antibody. Thereby, it becomes sortable.

It is particularly preferred that the surface marker fulfills at least one of the following requirements: The surface marker should be resistant to digestion with trypsin, or with papain, and should not be internalized by the cell upon binding of an antibody to the surface marker. It is preferred that the (sortable) surface marker fulfills all of the before mentioned requirements.

The surface marker is a protein that is not expressed in this form in a wild type cell, i.e. a cell that does not contain the sequence of the conditional transgenic surface marker. In a preferred embodiment of the invention, the surface marker is a protein that is expressed ectopically. Such a surface marker can be derived e.g. from a protein that is endogenously expressed in a wild type cell, such as from an intracellular protein (like a cytoplasmic or nuclear protein) or from a protein of the nuclear membrane. In another preferred embodiment of the invention, the surface marker is a protein that is expressed as a membrane bound or membrane associated protein in a wild type cell. In this case, this modified version of an endogenously expressed membrane protein does not fulfill the same function as the endogenously expressed protein, to enable the distinction between the endogenously expressed protein and the surface marker. In addition, such an endogenously expressed membrane protein also differs in the extracellular part of the protein from its wild type form in order to make it distinguishable for sorting of the cell. The modification of the endogenously expressed protein can be achieved by, for example, inserting or deleting at least one amino acid to generate a transmembrane or membrane association domain, by mutating a binding domain, the active center and/or an extracellular recognition domain.

Preferably, the surface marker comprises or is composed of an optional first tag sequence (TAG1) for intracellular positioning, linked to a transmembrane domain (TM) followed by a second tag sequence (TAG2) for extracellular positioning (in the direction from the N- to the C-terminus). The TAG2 sequence is preferably resistant to proteases generally used for tissue dissociation, like trypsin, papain, liberase, dispase and/or collagenase. It is furthermore preferred that TAG1 and TAG2 bind to their respective antibody both in their natural conformation as well as in a denatured conformation. TAG1 and TAG2 are preferably non-toxic. TAG2 can e.g. either be composed of the complete extracellular domain of CD271, CD4, H2Kk, CD2, CD14, CD90, CD45, or CD133 or of parts thereof. These parts are between 5 and 50, preferably between 10 and 40, most preferably between 15 and 30 or 20 and 25 amino acids long. These extracellular domains and parts thereof can also be proteins and peptides that are at least 50%, 60%, 70%, 80%, 90%, 95%, or 99% homologous to the extracellular domains and peptides named above. The extracellular domains of the proteins given above are known to a person of skill in the art or can be retrieved from an appropriate database.

In a preferred embodiment, TAG2 comprises, or is composed of, the CD133 extracellular loop 1 (SEQ ID NO 2) and/or the CD133 extracellular loop 2 (SEQ ID NO 3) or parts thereof (Miraglia et al. (1997) Blood, 90: 5013), including sequences that are at least 50%, 60%, 70%, 80%, 90%, 95% or 99% homologous thereto.

```
Sequence of CD133 (SEQ ID NO 1):
MALVLGSLLLLGLCGNSFSGGQPSSTDAPKAWNYELPATNYETQDSHKAG

PIGILFELVHIFLYVVQPRDFPEDTLRKFLQKAYESKIDYDKPETVILGL

KIVYYEAGIILCCVLGLLFIILMPLVGYFFCMCRCCNKCGGEMHQRQKEN

GPFLRKCFAISLLVICIISIGIFYGFVANHQVRTRIKRSRKLADSNFKD

LRTLLNETPEQIKYILAQYNTTKDKAFTDLNSINSVLGGGILDRLRPNII

PVLDEIKSMATAIKETKEALENMNSTLKSLHQQSTQLSSSLTSVKTSLRS

SLNDPLCLVHPSSETCNSIRLSLSQLNSNPELRQLPPVDAELDNVNNVLR

TDLDGLVQQGYQSLNDIPDRVQRQTTTVVAGIKRVLNSIGSDIDNVTQRL

PIQDILSAFSVYVNNTESYIHRNLPTLEEYDSYWWLGGLVICSLLTLIVI

FYYLGLLCGVCGYDRHATPTTRGCVSNTGGVFLMVGVGLSFLFCWILMII

VVLTFVFGANVEKLICEPYTSKELFRVLDTPYLLNEDWEYYLSGKLFNKS

KMKLTFEQVYSDCKKNRGTYGTLHLQNSFNISEHLNINEHTGSISSELES

LKVNLNIFLLGAAGRKNLQDFAACGIDRMNYDSYLAQTGKSPAGVNLLSF

AYDLEAKANSLPPGNLRNSLKRDAQTIKTIHQQRVLPIEQSLSTLYQSVK

ILQRTGNGLLERVTRILASLDFAQNFITNNTSSVIIEETKKYGRTIIGYF

EHYLQWIEFSISEKVASCKPVATALDTAVDVFLCSYIIDPLNLFWFGIGK

ATVFLLPALIFAVKLAKYYRRMDSEDVYDDVETIPMKNMENGNNGYHKDH

VYGIHNPVMTSPSQH

Sequence of the (extracellular) loop 1 of CD133
(SEQ ID NO 2):
NHQVRTRIKRSRKLADSNFKDLRTLLNETPEQIKYILAQYNTTKDKAFTD

LNSINSVLGGGILDRLRPNIIPVLDEIKSMATAIKETKEALENMNSTLKS

LHQQSTQLSSSLTSVKTSLRSSLNDPLCLVHPSSETCNSIRLSLSQLNSN

PELRQLPPVDAELDNVNNVLRTDLDGLVQQGYQSLNDIPDRVQRQTTTVV

AGIKRVLNSIGSDIDNVTQRLPIQDILSAFSVYVNNTESYIHRNLPTLEE

YDSYWW

Sequence of the (extracellular) loop 2 of CD133
(SEQ ID NO 3):
TFVFGANVEKLICEPYTSKELFRVLDTPYLLNEDWEYYLSGKLFNKSKMK

LTFEQVYSDCKKNRGTYGTLHLQNSFNISEHLNINEHTGSISSELESLKV
```

```
-continued
NLNIFLLGAAGRKNLQDFAACGIDRMNYDSYLAQTGKSPAGVNLLSFAYD

LEAKANSLPPGNLRNSLKRDAQTIKTIHQQRVLPIEQSLSTLYQSVKILQ

RTGNGLLERVTRILASLDFAQNFITNNTSSVIIEETKKYGRTIIGYFEHY

LQWIEFSISEKVASCKPVATALDTAVDVFLCSYIIDPLN
```

In an alternative preferred embodiment, TAG2 comprises or consists of, at least in part, an artificial sequence that has no homology to any existing mammalian sequence to avoid unwanted interactions or affinity to any known surface epitope:

```
                              (SEQ ID NO 4)
       NEGVYSDQ, (SEQ ID NO 5)
       DQNSQDEE, (SEQ ID NO 6)
       SDDEDQEQ,

DEYDHYVD,              (SEQ ID NO 7)
       and/or (SEQ ID NO 8)
       DFKDEDFKD.
```

TAG2 preferably does not internalize into the cell upon antibody reaction. All given DNA sequences are preferably codon optimized.

In another preferred embodiment, in order to avoid triggering of an immune response, an additional protease recognition sequence (PRS) is inserted between TM and TAG2. This PRS allows for a detachment of the transgenic surface epitope after sorting of cells and prior to grafting the cells into a recipient. PRS is composed in such a way that it is cleaved by a sequence specific protease which is naturally not present in the extracellular space of mammals. An example for a suitable protease is the tobacco etch virus NIa proteinase (Lucast et al. (2001) BioTechniques 30:544). This protease recognizes a specific heptapeptide sequence, E-X-X-Y-X-Q-S/G (SEQ ID NO 9), cleaving between Q and S/G and is active under a wide range of conditions and in the presence of various protease inhibitors (X: any amino acid). The cleaving site is compatible with trypsin (which cleaves after lysine, arginine and modified cystidine) and papain (which cleaves after basic amino acids, leucine and glycine), as it is resistant to both of these proteases.

Accordingly, the term "transgenic" is meant to refer to a protein that is not present in a wild type cell. Instead it can be generated through genetic modification, such as introduction of a transmembrane and/or membrane association domain.

The term "surface marker" or "reporter" is used herein to refer to an extracellular cell surface marker or an extracellular cell surface marker gene and/or fragment/-s and/or homologs thereof. The term "homolog" refers to sequences (of DNA, RNA, and/or protein) with at least 80% homology, preferably with at least 90%, most preferably at least 95% homology to the given sequence referred to inhere by their gene or protein names. The sequences referred to in the present invention include homologs without further mentioning.

The first transcription sequence (the STOP DNA) includes but is not limited to sequences which are signalling release of the nascent polypeptide from the ribosome due to binding of release factors in the absence of cognate tRNAs with anticodons complementary to these stop signals like the classical three stop codons: UAG (amber), UGA (opal, sometimes also called umber), and UAA (ochre) or complex assemblies of different sequences leading to a higher degree of transcription termination, like the "neostop" or "Westphal-Stop" consisting of the 3' portion of the yeast His3 gene, an SV40 polyadenylation sequence and a false translation initiation codon followed by a 5' splice donor site (Lakso M., Sauer, B., Mosinger, B. J., Lee, E. J., Manning, R. W., Yu, S. H., Mulder, K. L. and Westphal, H. (1992) Targeted oncogene activation by site-specific recombination in transgenic mice. Proc. Natl. Acad. Sci. USA, 89: 6232-6236).

There are two possible ways of excising the first transcription sequence to enable the expression of the surface marker, namely through a non-enzymatic reaction or through an enzymatic reaction. This is possible, e.g. through use of modified or tagged nucleotides that are introduced into the nucleic acid, which upon activation induce double stranded breaks into the nucleic acid. Consecutively, antibody mediated and proximity induced spontaneous double strand recombination leads to the excision of the first transcription sequence (STOP DNA).

In a preferred embodiment in which the excision is performed in an enzymatic manner, the first transcription sequence (STOP DNA) is flanked on each side by a recombinase recognition site (RRS). For the conditional removal of the first transcription sequence from the gene, a recombinase is needed that specifically recognizes the RRSs and excises the first transcription sequence so that the surface marker is generated. The expression of the recombinase can be constitutive or inducible. It is preferred that the RRSs are specific for a CRE recombinase or a FLP recombinase.

The term "recombinase" is used herein to refer to an enzyme that catalyzes site-specific recombination of DNA, specifically recognizing RRSs.

The activity of the recombinase leads (due to the excision of the STOP DNA) to a cell wherein the gene encoding a conditional transgenic surface marker comprises: a promoter, operably linked to a second transcription sequence encoding a surface marker suitable for cell sorting. Therefore, the result of the recombination reaction is a transgenic cell expressing the transgenic surface marker. As will be explained below, the enzymatic action of the recombinase renders the cell sortable on the basis of the expressed surface marker.

It is preferred that the second transcription sequence is a modified version of the human LNGFR gene, a modified version of the human CD4 gene, H2Kk, or CD133, whereby the term "modified" refers to a protein that has been mutated or truncated in its intracellular part in order to disrupt its signalling function.

In a preferred embodiment, the surface marker is the original or a modified version of CD271, CD4, H2Kk, CD2, CD14, CD90, CD45, CD133, or a homolog thereof or any protein comprising at least one transmembrane and/or membrane associated domain stemming from a transgenic gene. In another preferred embodiment, the surface marker is a protein comprising at least one transmembrane and/or membrane associated domain and is being located in the cell membrane such that at least a part of the protein is on the extracellular surface and the protein is not expressed endogenously but is expressed ectopically or is a modified version of an endogenously expressed protein whereby the modified version does not fulfill the same function as the endogenously expressed protein.

The promoter can be a heterologous promoter, a ubiquitous or tissue specific promoter, and/or a constitutive or inducible promoter. It is preferred that the promoter is the promoter of the following genes: actin, hCMV, PGK, FABP, Lck, CamKII, CD19, Keratin, Albumin, aP2, Insulin, MCK, MyHC, WAP, Col2A, Mx, ROSA26, tet or Trex or an assembly of multiple promoter and enhancer elements like the CAGGS promoter. It is preferred that the promoter leads to a strong expression of the surface marker in all cell types, so that the number of surface marker molecules on the cell surface is sufficient for detection and sorting.

The usage of an inducible promoter is preferred, in particular when sorted cells are grafted into recipients and an immune response needs to be avoided. To this end, the transgenic surface epitope is eliminated prior to grafting by using a sequence specific protease cleaving the PRS (see above) and a reexpression of the surface epitope is avoided by not inducing the inducible promoter.

It is also possible that the promoter is an endogenous promoter. Thereby the surface marker is expressed in the same way as the endogenous gene that is or was under the control of that particular promoter in the cell. It is furthermore preferred that the promoter of the surface marker in the form of a modified endogenous protein is identical to the promoter that drives the expression of that endogenous protein. Thereby the surface marker is expressed in the same way as the endogenous gene the surface marker is derived from. The expression of the surface marker thereby follows the same spatiotemporal and cell specific pattern as the expression of the corresponding endogenous gene. This allows for the study of cell specific and spatio-temporal expression of a protein in a cell.

The cell can further contain a recombinase, which is driven by an inducible promoter and/or the promoter of the endogenous cell type specific marker.

The invention also relates to the use of a cell as described above and herein for the sorting of cells.

The invention also pertains to a tissue, an organ or an organism or a line of an organism containing a cell as described above and herein. A preferred organism is a mammal, in particular a rodent, such as a mouse, rabbit or a rat, or a pig, a cattle, a sheep, a dog, a cat, or a monkey. A preferred tissue or organ is also from a human.

Cells, cell lines or transgenic organisms expressing a cell surface marker or reporter can then be used as magnetically sortable entities in co-cultures or other organisms where they are introduced by e.g. methods comprising grafting, transplantation, injection, inoculation, and/or administration.

The problem underlying the present invention is also solved by providing a construct, in particular a recombination construct for generating a transgenic cell as described above and herein. Such a construct contains a gene encoding a conditional transgenic surface marker comprising
(i) a promoter, operably linked to
(ii) a first transcription sequence (STOP DNA), and
(iii) a second transcription sequence encoding a surface marker,
whereby the first transcription sequence prevents the transcription of the second transcription sequence and is also conditionally excisable such that the second transcription sequence can be transcribed to yield a transgenic cell expressing the conditional transgenic surface marker, and whereby the surface marker renders the cell sortable through the detection of the conditional transgenic surface marker.

The second transcription sequence encoding the surface marker comprises or contains
  (a) optionally, a first tag sequence for specifically binding to an antibody positioning at the cytosolic face of the plasma membrane of a cell, or
  (b) a transmembrane or membrane association domain for positioning (anchoring) the surface marker in the cell membrane, such that the surface marker can be detected from the extracellular side; and (c) a second tag sequence for rendering a cell sortable, in particular by specifically binding on the extracellular side of a cell to an antibody.

The first tag sequence or the transmembrane or membrane association domain can in one embodiment at least partially overlap with the second tag sequence.

In one embodiment of the invention, this construct is an epigenetic vector. In an alternative embodiment, the construct is a vector that integrates into the genome of a cell (recombination construct). Accordingly, the surface marker is expressed either from an epigenetic vector or from within the genome of the cell. It is noted that a construct that has been integrated into the genome of the cell is still referred to herein as a construct. A person of skill in the art will readily be able to distinguish between a construct that has or has not been integrated into the genome.

In order to facilitate the introduction of a recombination construct according to the invention into the genome of the cell through homologous recombination, the recombination construct also comprises a first sequence portion located upstream of the gene and a second gene sequence located downstream of the gene. The first sequence portion and the second sequence portion are homologous to corresponding sequence portions of the genomic sequence at the locus targeted for integration. Details of the requirements for such sequences are known to a person of skill in the art.

The invention further pertains to the use of a (recombination) construct as described above and herein for generating a cell containing a gene encoding a conditional transgenic surface marker that is detectable on the surface of the cell.

It is of advantage that a transgenic reporter system as described herein can be used in combination with different existing cells, cell lines or transgenic organisms expressing a recombinase for sorting many different cell types.

The underlying problem is also solved by a method for generating a cell as described above and herein, comprising introducing a (recombination) construct as described above and herein into a cell.

In this method, it is preferred to express a recombinase in a constitutive or inducible manner in the cell. This expression of the recombinase can be achieved by transferring a constitutive or inducible recombinase gene into the cell, e.g. using transfection, viral transduction, lipofection, electroporation, injection or combinations thereof. In the case that an organism is present containing a recombination construct as described above and herein in its genome that does not express a recombinase to excise the first transcription sequence blocking transcription of the surface marker, it is possible to cross the organism with an organism carrying a constitutive, inducible and/or cell type specific recombinase and selecting an offspring cell carrying both the transgene and the recombinase in order to enable the recombination event.

The already existing and extensively characterized recombinases and transgenic organisms expressing a recombinase can be used to magnetically sort those cells, cell lines or transgenic organisms which are defined by the promoter driving the recombinase expression and/or being defined by spatio-temporal properties (Sauer et al. (1988) Proc Natl Acad Sci USA 85:5166-5170), as will become evident together with the description below.

The possibility of using well characterized transgenic mice expressing a recombinase together with a mouse carrying cells of the present invention provides for the convenient generation of transgenic mice carrying both transgenes, namely through crossing of the mice with each other.

The recombinase gene can be introduced into the reporter system for the recombination event by different methods, including but not limited to transfection, electroporation, injection, or crossing of cells, cell lines or transgenic organisms with a second biological entity or an organism expressing a constitutive or inducible recombinase in at least some cells.

Alternative to the expression of a recombinase, a recombinase protein can be introduced into the cell, e.g. through transfection, electroporation, transfer using packaging material like micelles, injection or combinations thereof. Alternatively, a permeable version of a recombinase like protein tagged with a protein transduction domain, e.g. the TAT sequence (Nolden et al. (2006) Nat. Methods 3: 461-467) can be used.

The underlying problem is furthermore solved by a method for generating a transgenic organism. This method comprises introducing a construct, in particular a recombination construct as described above and herein into a cell, e.g. by injecting it, preferably into the nucleus, or using transfection etc., and propagating the cell under conditions that allow for the development of an organism.

In one embodiment of this method, it is e.g. possible to generate transgenic cells in a mouse by heterologous or homologous recombination of the construct in embryonic stem (ES) cells (gene targeting). In this case, the cell is an embryonic stem cell that is placed into a blastocyst which is implanted into a surrogate mother.

In another embodiment of this method, it is e.g. possible to generate transgenic cells in a mouse through pronucleus injection by introducing the recombination construct into the pronucleus of an oocyte which is implanted into a surrogate mother.

In a further embodiment of this method, it is e.g. possible to generate transgenic cells in a mouse by somatic cell nucleus transfer pronucleus injection (cloning). In this case, the introduction of the recombination construct of the method further comprises the steps of removing the nucleus of the cell containing the (recombination) construct, removing the nucleus of an oocyte, and inserting the nucleus of the cell containing the recombination construct into the oocyte which is implanted into a surrogate mother. Then, the cell is propagated under conditions that allow for the development of an organism. Such an organism is preferably a mammal, in particular a rodent, such as a mouse or a rat.

The underlying problem is also solved by a method for separating a cell from a population of cells, whereby the cell to be separated is a cell as described above and herein (containing a gene encoding a conditional transgenic surface marker suitable for cell sorting that is detectable on the surface of the cell), and whereby the gene encoding the conditional transgenic surface marker is not contained in other cells of the population. Therefore, the other cells are not able to express an identical surface marker.

The method is based on the findings that cells being characterized by the specific expression of an intracellular marker or by spatio-temporal parameters can be sorted by magnetic cell sorting if a transgenic cell, cell line or transgenic organism is obtained in which an inducible promoter and/or the promoter of the intracellular marker is used to drive the expression of an extracellular cell surface marker or reporter. The present invention therefore allows separating cells by cell sorting, in particular by magnetic cell sorting that were not accessible to these methods before, due to their lack of a surface marker that is essential for the sorting procedure.

This method comprises the steps of expressing the conditional transgenic surface marker so that it becomes detectable on the surface of the cell to be separated, but not on the other cells of the population, by removing the first transcription sequence if present, and separating the cell from the population by means of the expressed conditional transgenic surface marker.

Preferably, the separation is performed by adding an antibody to the population of cells that specifically binds to an extracellular epitope of the conditional transgenic surface marker. It is advantageous that the antibody is labeled with a detectable agent suitable for cell sorting (cell separation), such as a fluorescent dye or a magnetically responsive agent.

It is preferred that the antibody is coupled to a magnetically responsive agent, whereupon the antibody can be used to separate the cell bound to it under conditions sufficient to specifically bind the antibodies to the epitope (antigen).

In a preferred embodiment, the method further comprises the following steps: immobilizing the cell expressing the conditional transgenic surface marker that is specifically bound to the antibody labeled with a magnetically responsive agent in a ferromagnetic matrix through a magnetic field; washing the matrix to remove unbound cells; and removing the magnetic field to elute the cell from the matrix. Thereby, a cell sample enriched in or consisting of transgenic cells is provided.

The elution of the ferromagnetic matrix can be performed using gravity flow, centrifugation, vacuum filtration or by positive pressure, e.g. using a plunger.

The term "magnetic cell sorting" is used herein to refer to procedures for cell separation (cell sorting) including, but not limited to, magnetic separation using antibodies linked to colloidal magnetic particles, affinity chromatography and cytotoxic agents joined to a monoclonal antibody or used in conjunction with any antibody-dependent separation technique known in the art. In addition, biological entities may be separated by "panning" with an antibody attached to a solid matrix, e.g. to a plate. Fluorescence activated cell sorting (FACS) may also be used and may have varying degrees of color channels, low angle and obtuse light scattering detecting channels, and impedance channels. Any ligand-dependent separation techniques known in the art may be used in conjunction with both positive and negative separation techniques that rely on the physical properties of the cells, cell lines or transgenic organisms rather than antibody affinity, including but not limited to elutriation and density gradient centrifugation.

Methods to separate cells are commercially available e.g. from Invitrogen, Stem cell Technologies, in Cellpro, Seattle or Advanced Magnetics, Boston. For example, autologous monoclonal antibodies can be directly coupled to magnetic polystyrene particles like Dynal M 450 or similar magnetic particles and used e.g. for cell separation. Alternatively, antibodies can be biotinylated or conjugated with digoxigenin and used in conjunction with avidin or anti-digoxigenin coated affinity columns. In a preferred embodiment however, monoclonal antibodies are used in conjunction with colloidal superparamagnetic microparticles having an organic coating by e.g. polysaccharides (Miltenyi et al. (1990) Cytometry 11:231-238). These particles can be used having a size of 10 to 200 nm, preferably between 40 and 100 nm, and can be either directly conjugated to autologous antibodies or used in combination with anti-immunoglobulin, avidin or anti-hapten-specific microbeads. Polysaccharide-coated superparamagnetic particles are commercially available from Miltenyi Biotec GmbH, Germany.

In result, the method provides an extracellular cell surface marker that indicates the expression of an internal marker and/or a spatiotemporal property and allows the direct or indirect sorting of cells including, but not limited to, magnetic sorting, flow sorting and/or immunopanning.

In further embodiments of the invention, cells, cell lines or transgenic organisms that could not be magnetically sorted so far due to their lack of extracellular markers or reporters are sortable by the methods of the present invention including but not limited to the following cell (sub-) types: astrocytes (general and time dependent) (GFAP promoter), general differentiated neurons (synapsin promoter), dorsal root ganglia (synapsin promoter), dopaminergic, gabaergic, serotonergic, catecholaminergic, parvalbumin, or calretinin positive neurons, hepatic stern cells (GFAP), hepatocytes, kupfer cells, keratinocytes (K14), pancreatic islet cells (insulin), adipocytes, cardiomyocytes, treatment (drug) specific or pathological cells like reactive cells (astrocytes, hepatic stern cells etc.), metabolizing cells (enzyme activity), region specific cell using light inducible promoter and/or time dependent cell states using e.g. doxycycline inducible promoter.

The underlying problem is also solved by a kit for separating a cell as described above and herein from a population of cells. Such a kit comprises a recombination construct as described above and herein, and an antibody specific for an extracellular epitope of the conditional transgenic protein that is detectably labeled. The label can be a magnetic or a fluorescent label. Preferably, the antibody is coupled to a magnetically responsive reagent.

The kit may also contain a recombinase protein or a construct (vector) for expressing a recombinase as well as further reagents or enzymes.

The invention also refers to an antibody that specifically binds to a conditional transgenic surface marker as described above and herein. In a preferred embodiment, the antibody specifically binds to the second tag sequence of the surface marker that function in rendering a cell in which it is expressed sortable. In another preferred embodiment, the antibody specifically binds to a peptide with a sequence selected from the group consisting of SEQ ID NOs 1 to 9 or a part thereof or a homolog of any of the beforementioned sequences. The antibody can be both monclonal or polyclonal. Methods for generating antibodies are known in the art (e.g. Köhler and Milstein (1975) Nature 256, 495-497).

The features of the invention disclosed in the previous description, the claims and the figures can be significant individually as well as in any combination for the realization of the invention in its various embodiments.

The invention described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

DESCRIPTION OF THE DRAWINGS

In the accompanying drawings, which are provided to illustrate the invention.

SEQUENCES

```
SEQ ID NO 1:    CD133

SEQ ID NO 2:    loop 1 of CD133

SEQ ID NO 3:    loop 2 of CD133

SEQ ID NO 4-8:  TAG2

SEQ ID NO 4:    NEGVYSDQ (SEQ ID NO 4),

SEQ ID NO 5:    DQNSQDEE

SEQ ID NO 6:    SDDEDQEQ

SEQ ID NO 7:    DEYDHYVD

SEQ ID NO 8:    DFKDEDFKD

SEQ ID NO 9:    protease recognition sequence (PRS) of the tobacco etch virus

NIa proteinase: E-X-X-Y-X-Q-S/G
```

Examples

Cloning of the ROSA26 Targeting Vectors

To allow the expression of a surface marker upon Cre-mediated excision of a STOP cassette, a suitable transgene had to be placed under control of a strong and ubiquitously expressed promoter. Different promoter/reporter combinations were tested by measuring their respective expression levels in transfected cell lines. As surface epitopes different genes were chosen for comparison where antibody coupled beads are already available: human prominin, human CD4, and the truncated human LNGFR (CD271, p70). The GAGG (Cytomegalo-Virus-ieEnhancer, Chicken β-Actin-Promoter, Rabbit β-Globin Intron and Splice Acceptor) promoter combined with the ΔhLNGFR- or H2Kk-epitope performed best in transfected 1881 cells as well as in primary neurons and was therefore chosen for the targeting constructs.

Figure 1:
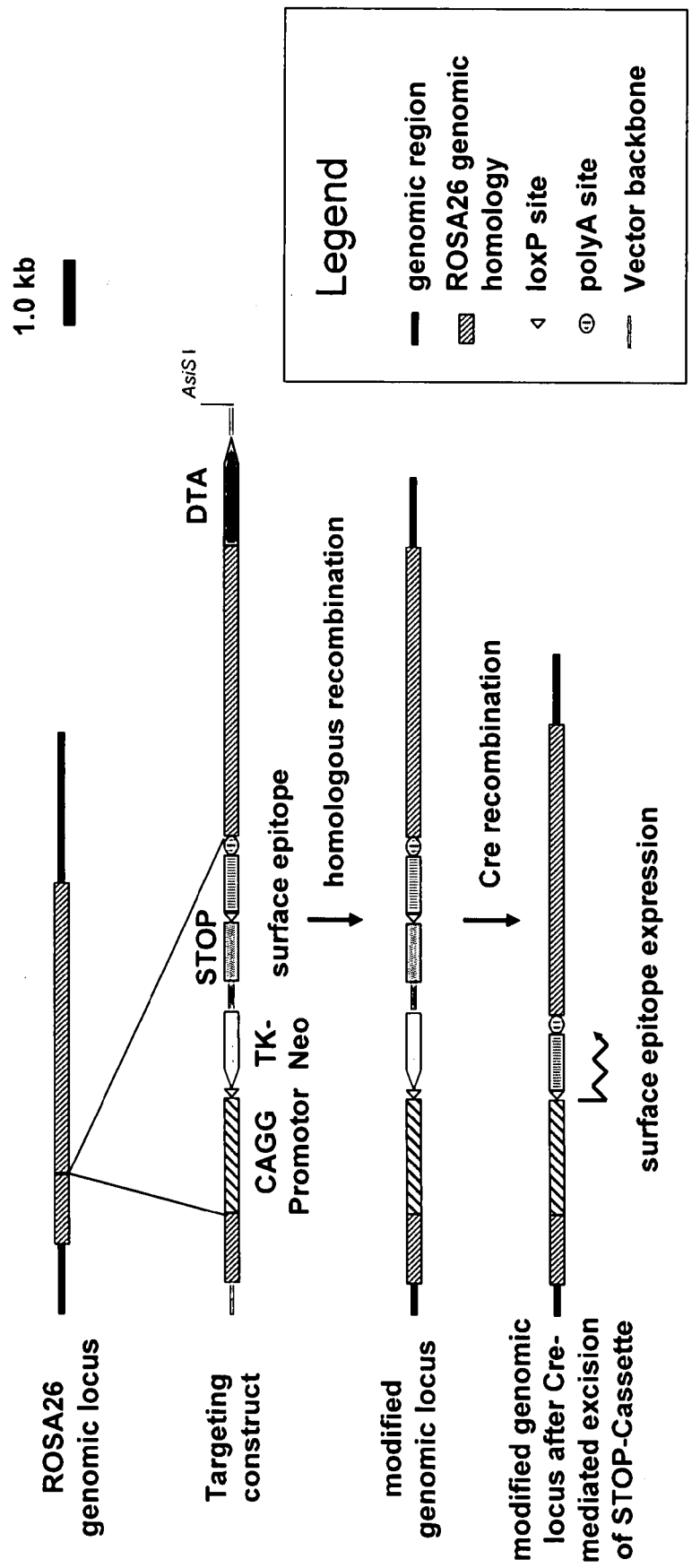
FIG. 1: displays the cloning strategy for the targeting construct, the targeting construct, the modified genomic locus as well as modified genomic locus after recombinase mediated excision of the STOP-cassette.

In order to achieve a defined and inducible expression of the reporter, a knock in gene targeting approach was used. The Gt(ROSA)26Sor locus (also known as ROSA26) was already successfully used for the expression of reporter genes upon cre-mediated removal of STOP cassettes (Zambrowicz et al. (1997) Proc Natl Acad Sci USA. 94:3789-94; Mao et al (1999) Proc Natl Acad Sci USA 96:5037-42). For the knock in approach several targeting vectors, iSE-TV (inducible surface epitope targeting vector), containing different inducible surface epitopes were constructed: iSE-LNGFR-TV; iSE-LNGFR-EGFP-TV; iSE-H2Kk-TV; iSE-H2Kk-EGFP-TV. All targeting vectors contained a TK-NEO gene (for positive selection) and a STOP-Element flanked by loxP-sites and homology arms to target the ROSA26 locus, a CAGG promoter upstream of the first loxP-site, the coding regions of the respective reporter(s) downstream of the second loxP-site and the DTA gene downstream of the homology arm (for negative selection) (FIG. 1). In case an enhanced green fluorescent protein (EGFP) element was included, it was placed behind an internal ribosomal entry side (IRES) driving the expression of the EGFP.

The basic vector STOP-ROSA-TV, containing a Stop-Element flanked by loxP-sites and homology arms to target the ROSA26 locus was used as a starting vector (Kuhn et al. (1995) Science 269: 1427-9). To integrate the CAGG promoter upstream of the first loxP-site, vector DNA was digested with PacI (NEB). Overlapping bases were removed using T4-DNA-Polymerase (Invitrogen) and dephosphorylation was done using Alkaline Phosphatase (Roche) to avoid self ligation. The CAGG promoter was isolated from a vector by restriction digestion with MluI and BglII (both NEB) and gel extraction (NucleoSpin® Extract II Kit, Macherey Nagel) of the resulting 1.7 kB band. After blunting of the restriction sites (T4-DNA-Polymerase, Invitrogen), the DNA fragments were ligated using the Rapid DNA Ligation Kit (Roche) and transformed in competent DH5α E. coli (Invitrogen). Quality control of the resulting vector CAGG-ROSA-TV was done by restriction analysis and sequencing. The coding regions of truncated LNGFR and H-2KK were amplified by PCR from pMACS KK and pMACS LNGFR (both Miltenyi Biotec), digested with AscI and XmaI and purified by gel extraction. To maintain an IRES-EGFP element downstream of the LNGFR or H-2KK coding regions, alternative primers were used and the PCR fragments were only digested using AscI. After dephosphorylation of the digested vector CAGG-ROSA-TV, it was ligated either with LNGFR or H-2KK DNA fragments. After transformation in competent DH5α E. coli and quality control, plasmid DNA was isolated in large scale using NucleoBond® Xtra EF Maxi Kit (Macherey Nagel). Before electroporation, the targeting vectors were linearized using AsiSI (NEB).

Preparation of a Gene Targeting Construct for Electroporation of ES Cells

The iSE-TVs were linearized by restriction enzyme digestion, phenol/chloroform extracted, precipitated, and resuspended in phosphate buffered saline (PBS). Concentration was determined by OD measurement. Complete digestion and integrity of the linearized gene targeting constructs were visualized by agarose gel electrophoresis.

Electroporation

For electroporation, mouse embryonic stem (ES) cells were thawed and expanded for at least one passage. ES cells were cultured in a medium containing 90% GMEM (Invitrogen), 5 FCS (Biowest), 5% NCS (Harlan Sera-Lab), 1 mmol/l sodium-pyruvate (Invitrogen), 1×NEA (Invitrogen), 0.5× pen/strep (Invitrogen), and 1000 U/ml LIF (ESGRO)) on gelatine (0.1% G-2500, Sigma) coated dishes without feeder cells at 37° C. and 5% $CO_2$. Cells were passaged using 0.05% Trypsin/EDTA (Invitrogen). $1\times10^7$ ES cells were mixed with 30 µg of linearized iSE-TV and after a 10 minute incubation on ice transferred to the electroporation cuvette for electroporation (BioRad Gene Pulser II, 200 V, 500 µF). After the pulse, the ES cells were once more incubated on ice for 10 minutes, and then transferred into ES cell medium, plated onto four gelatinized 9 cm tissue culture dishes, and fed daily.

Selection and Screening of ES Cells

Two days after electroporation, selection was started by adding 200 µg/ml G418 to the culture medium. After 8-10 days of selection, when all colonies on a control plate had died and clearly visible ES cell colonies appeared. Colonies were isolated, trypsinized, and plated on gelatinated 96 well tissue culture dishes. Subconfluent wells were split on one gelatinized 96 well master tissue culture dish for freezing and two gelatinized 96 well replica tissue culture dishes for genomic DNA isolation. The ES cells were lysed, the genomic DNA precipitated, and resuspended in 50 µl $H_2O$ in the 96 well tissue culture dishes. For screening, 1 µl of the genomic DNA was used in a nested PCR reaction. PCR positive colonies were confirmed by Southern Blot hybridization of 3 µg of appropriate linearized genomic DNA with an internal (neo) probe.

In case of the iSE-LNGFR-TV, 192 clones were picked from 2 electroporations and 128 clones were screened by PCR resulting in 12 positive clones (iSE-STOP-LNGFR-ES) which where additionally re-screened positive for homologous integration and negative for heterologous integrations by Southern-Blot.

For the iSE-LNGFR-EGFP-TV, 192 ES cell clones where picked and 112 screened resulting in 12 positive clones (iSE-LNGFR-EGFP-ES). For the iSE-H2Kk-TV, 480 clones where picked and 480 screened resulting in 7 positive clones (iSE-H2Kk-ES).

In Vitro Functionality Test of iSE-ES Cells

Figure 2:
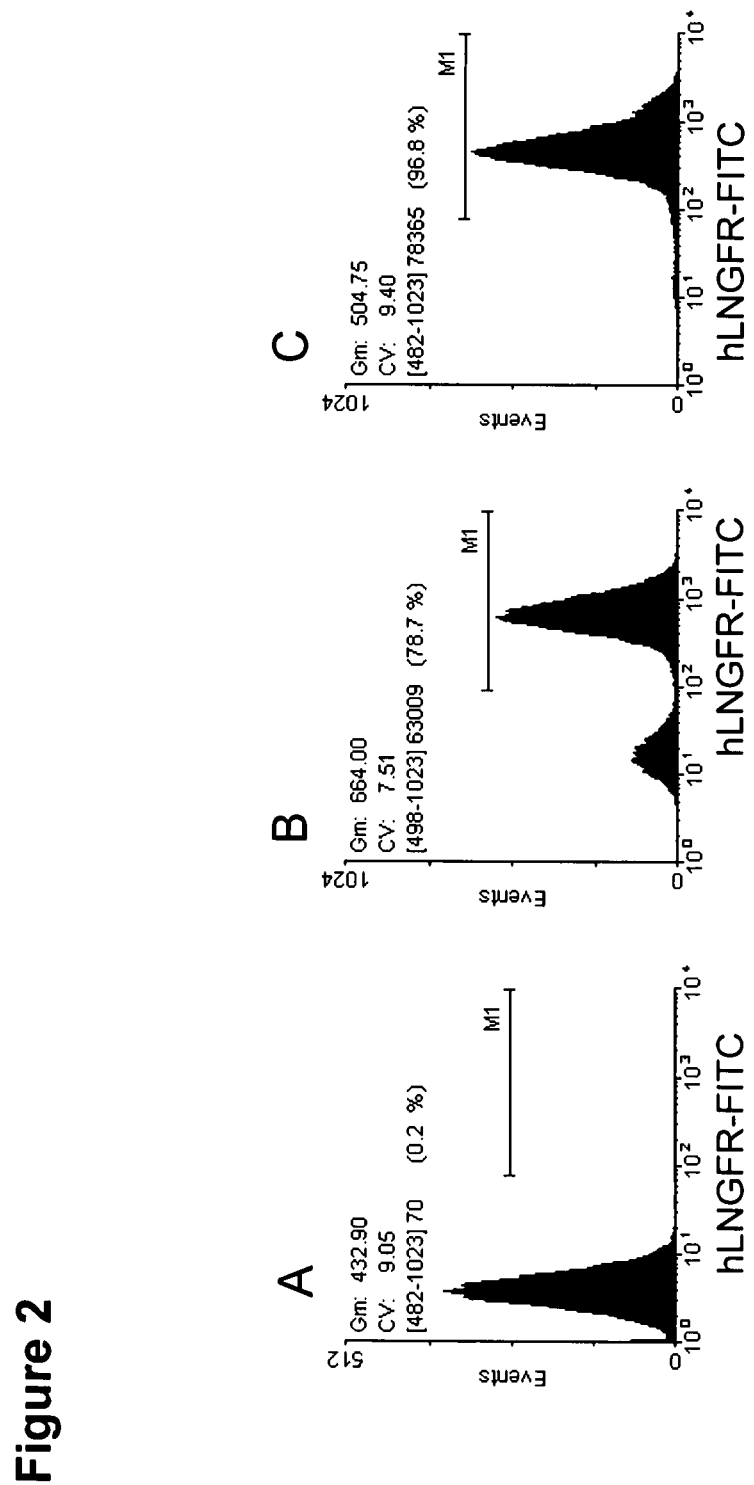
FIG. 2: displays the flow cytometric analysis of the expression of LNFGR in iSE-LNGFR-EGFP-ES prior (A), after a first (B) and a second (C) enrichment step by MACS using MACSelect $K^k$ MicroBeads (Miltenyi). Cells were stained with CD271 (LNGFR)-FITC. Between the first and the second MACS enrichment, cells were cultivated for seven days.

To test whether the iSE-ES cells were functional, the iSE-STOP-LNGFR-EGFP-ES as well as the iSE-STOP-H2Kk-ES were electroporated with different vectors coding for the Cre gene. The Cre electroporated iSE-ES-cells were subjected to FACS analysis before and after MACS enrichment using the respective antibody coated beads. For example, in case of the iSE-LNGFR-EGFP-ES it was shown, that after the transfection with a Cre expressing vector, 0.2% of the ES cells were LNGFR positive (FIG. 2A). After a first round of MACS the percentage of LNGFR expressing clones could be raised to 79% (FIG. 2B). After 7 days of cultivation and a second round of MACS selection the percentage of LNGFR expressing clones was 97% (FIG. 2C). This example shows that the inserted construct is functional with respect to cre-recombination and surface expression and the LNGFR expressing clones can be enriched by MACS. Therefore, iSE-STOP-LNGFR-EGFP-ES cells can for example be used as a reporter line allowing to monitor the transient expression of a Cre recombinase and to sort fr cells which have undergone a recombination event.

Figure 3:
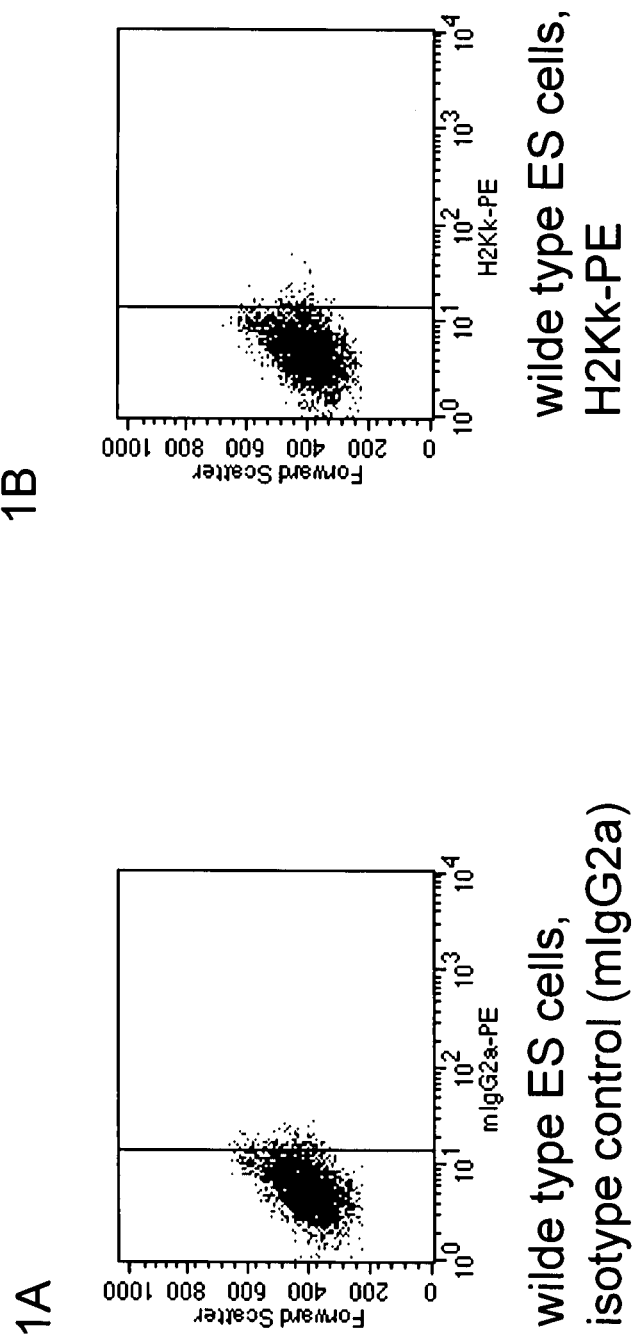
FIG. 3: depicts the expression of H-2Kk in wild type ES cells which were used for the generation of iSE-H2Kk-ES. A, Isotype control, staining with mIgG2a-PEB; B staining with anti-H-2Kk-PE (Miltenyi).
Figure 4:
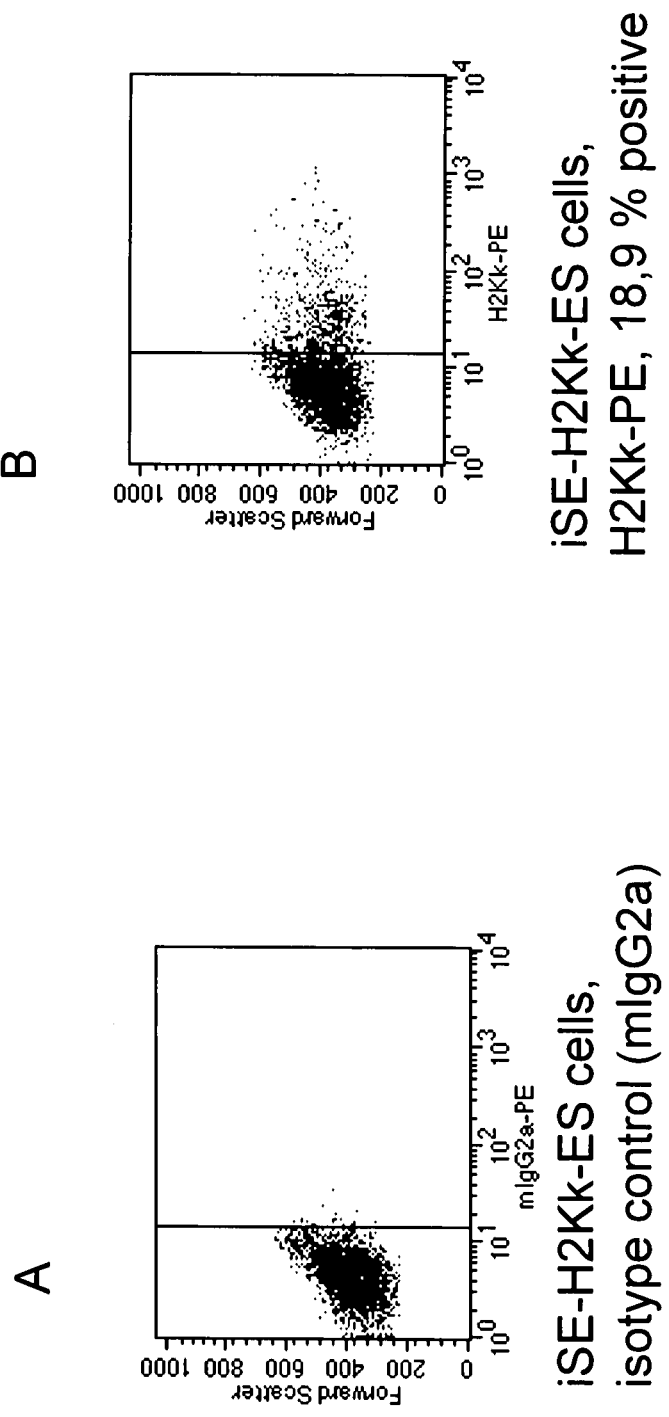
FIG. 4: depicts a representative flow cytometry analysis of iSE-H2Kk-ES, cultured under standard ES-cell culture conditions. 18.9% of the cells express the H2Kk-transgene in this experiment (stained with anti-H-2Kk-PE) (B), whereas no positive cells were detected in the isotype control staining (A).

In a second example, iSE-H2Kk-ES cells were generated by cre recombination mediated excision of the STOP sequence as described above and herein. It is known from the literature that MHCI expression of pluripotent embryonic stem cells is rather low. Therefore it was also expected to find no or only a dim H2Kk expression as it depends on the endogenous beta-2 microglobulin expression. After Cre recombination clones were subcloned and screened for H2Kk expression. One iSE-H2Kk-ES clone showing H2kk expression was further expanded and analyzed. While wild type ES cells did not show any H2Kk expression (FIG. 3), between 10% and 20% of the transgenic iSE-H2Kk-ES cells were H2Kk-positive (FIG. 4). This again demonstrates the functionality of the H2Kk knock in gene and the possibility to sort cells using a recombined transgenic surface marker.

ES-cells carrying the attenuated LNGR or H2Kk surface marker as well as the recombined surface marker did not show any differences to wild type ES-cells (e.g. with respect to doubling rate, morphology or induced as well as spontaneous differentiation behavior).

Analysis of H2Kk Expression on iSE-H2Kk-ES Cells

Figure 5:
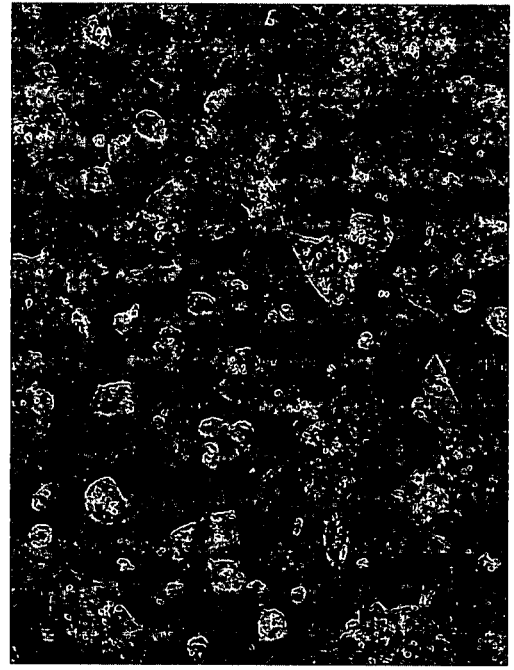
FIG. 5: shows H2kk$^-$ $^{iSE-H}$2Kk-ES cells and H2kk$^+$ iSE-H2Kk-ES cells after dividing both subpopulations using MACS and replating them for 2 days.
Figure 5:
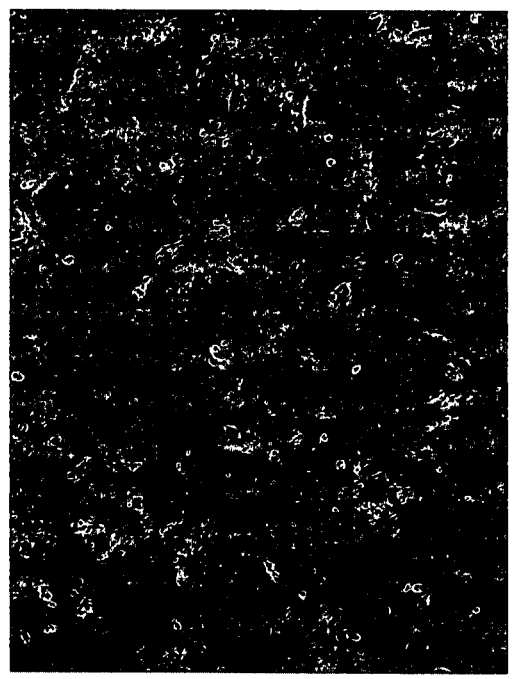

To further analyze the difference between H2kk$^+$ and H2kk$^-$ iSE-H2Kk-ES cells, both subpopulations were divided by magnetic cell sorting using H2Kk Microbeads (Miltenyi) following the instructions of the manufacturer. The purity of positively enriched H2kk$^+$ iSE-H2Kk-ES cells was in the range of 90% and the recovery 50% while the purity of the negatively selected H2kk$^-$ iSE-H2Kk-ES cells was again in the range of 90% and the recovery 60%. Both fractions, the positively enriched H2kk$^+$ iSE-H2Kk-ES cells as well as the flowthrough containing the H2kk$^-$ iSE-H2Kk-ES cells were replated. Subsequently the H2Kk expression was monitored and their morphology appearance inspected visually and by flow cytometric analysis for a period of 7 days (2 passages). After 2 days, H2kk$^-$ iSE-H2Kk-ES cells showed a morphology resembling an undifferentiated stage while the H2kk$^+$ iSE-H2Kk-ES cells had a higher granularity (also observed in the SSC of flow cytometry analysis) and less uniform colonies pointing to a partially spontaneous differentiation (FIG. 5). This example suggests a positive correlation between H2kk expression and differentiation stage of the iSE-H2Kk-ES cells.

Figure 6:
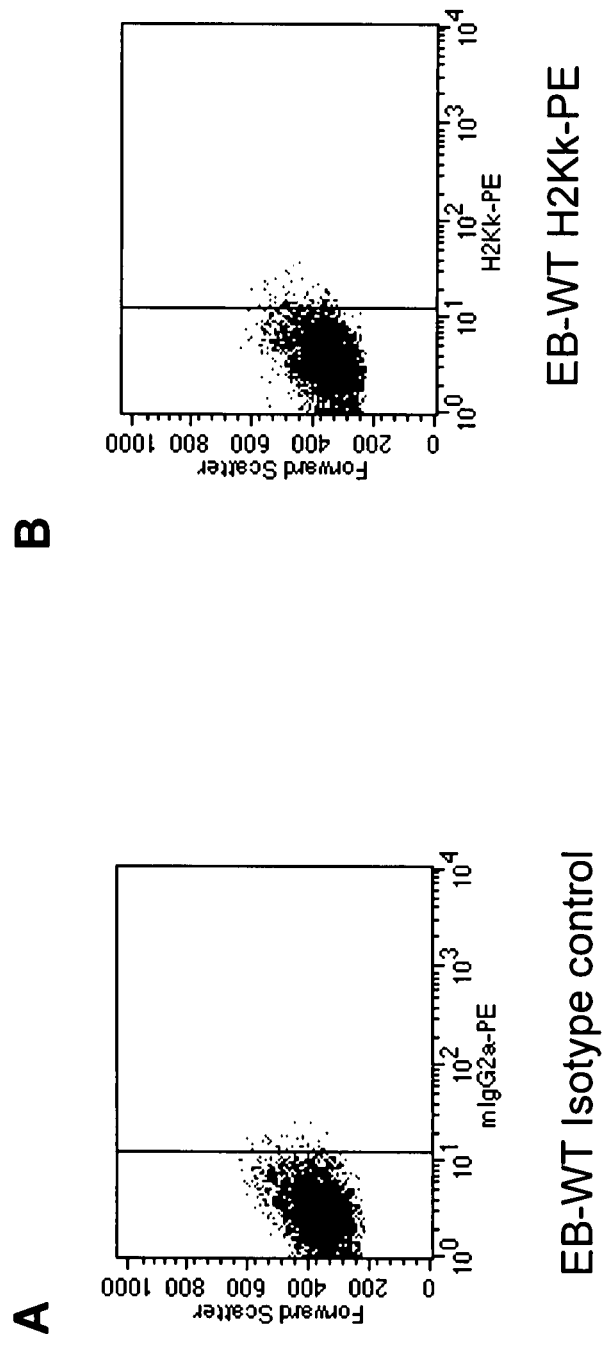
FIG. 6: shows representative flow cytometry analysis of wild type ES cells after 4 days of in vitro differentiation as described in the examples. No positive cells were detected in WT cells (B) and the respective isotype control staining of WT cells (A).
Figure 7:
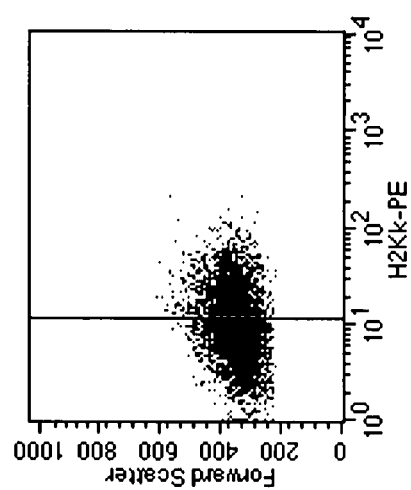
FIG. 7: shows representative flow cytometry analysis of iSE-H2Kk-ES cells after 4 days of in vitro differentiation as described in the examples. 39.5% of the cells expressed the H2Kk-transgene in this experiment (D), whereas no positive cells were detected in the isotype control staining (C), respectively.
Figure 7:
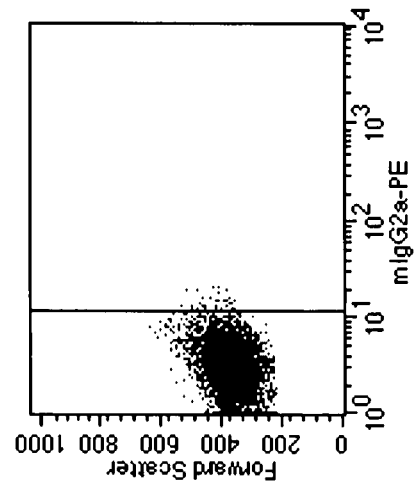

Analysis of H2Kk Expression on iSE-H2Kk-ES Cells Differentiating to Endoderm Progenitor Cells As already mentioned above, undifferentiated embryonic stem cells show little MHCI expression and therefore only dim expression of the transgenic marker H2Kk while for example a second transgenic marker LNGFR is expressed on all undifferentiated ES cells. To asses the dependency of H2Kk expression with respect to the differentiation state of iSE-H2Kk-ES cells, in vitro differentiation experiments where carried out, under conditions which promote differentiation to definitive endoderm progenitor cells as described elsewhere (Gouons-Evans et al. 2006). Briefly, cell colonies of iSE-H2Kk-ES cells and wild type ES cells (control) were trypsinized, and seeded at 20000 or 50000 cells/ml in serum-free differentiation medium (SFM) into bacterial grade petri dishes to allow embryoid body (EB) formation. At day 2 of differentiation EBs were harvested by sedimentation, dissociated with 0.05 Trypsin/EDTA (Invitrogen) and reaggregated in new SFM containing 5 µg/ml Activin A (R&D Systems) in twice the volume initially used at day 0. At day 4 of differentiation, EBs were collected by sedimentation, dissociated with 0.05% Trypsin/EDTA (Invitrogen), washed in DPBS (Invitrogen), and after centrifugation incubated in FCR blocking reagent, mouse (Miltenyi Biotec) and PEB (PBS, EDTA 2 mmol/l, BSA 0.05%) according to the manufacturers instructions. H2Kk-PE (Miltenyi Biotec) antibody titers were determined by titration and control samples were labeled using the same concentration of a PE-labeled control antibody of the same isotype (isotype control mouse IgG2a, Miltenyi Biotec). Flow cytometry measurements were conducted with a FACSCalibur flow cytometer (Beckton Dickinson). Dead cells were excluded from analysis by positive propidium iodide staining and according to scatter properties. After 4 days of in vitro differentiation, the ratio of H2Kk expressing cells was substantially increased to between 40% and 60% (FIG. 6 and FIG. 7). These results imply that differentiated cells have a better capability to express the H2kk transgene than ES cells when cultured under standard conditions.

Blastocyst Microinjection and Generation of Inducible Surface Epitope Mouse Lines (iSE-Ml)

For the generation of coat color chimeric mice, positively tested ES cell clones were thawed, expanded and after harvest provided in Hepes-buffered blastocyst injection medium. The 3.5 day-old blastocysts were obtained from superovulated mice of the strain C57Bl/6 by flushing the isolated uteri with M2 medium. An average of 12 ES cells were injected into each blastocyst in M2 medium. For incubation (37° C., 5% $CO_2$, saturated humidity), embryos were transferred to M16 medium. After recovery from injection, surviving and fully reconstituted blastocysts were retransferred in M2 medium into the uteri of pseudopregnant foster mothers of the CD1 mouse strain.

The offspring of the recipient females was raised and the coat color chimeric males were backcrossed to C57Bl/6 females to determine germline transmission of the ES cells. Brown offspring were genotyped as the ES cells by PCR and Southern Blot analysis. Heterozygous mice were further backcrossed to the C57Bl/6 background for line maintenance, or intercrossed with each other to generate homozygous mice, or mated with Cre expressing mice for analysis of recombination events and sorting of certain cell types.

Blastocysts were injected with the different iSE-ES cells. For example, two independent H2Kk ES-cell clones were injected into 246 blastocysts resulting in 107 offspring including 33 coat chimera. Three germ line chimera (iSE-STOP-H2Kk-Ml) were obtained which carry the transgene and were viable. These mice were backcrossed with wild type mice as well as intercrossed to obtain heterozygous and homozygous mouse lines respectively.

Mouse Maintenance

The mice at Miltenyi Biotec GmbH are housed in a SPF (specific pathogen free, according to the FELASA recommendations) barrier facility with a 12 hours light cycle in filter top cages which are changed once a week.

Generation and Analyses of iSE-mK14-H2Kk-ML and iSE-fK14-H2Kk-Ml

The iSE-H2Kk mice were crossed with male and female K14-Cre mice (Pasparakis et al. (2002) Nature 417: 861). The female K14-Cre (fK14) mice carry the Cre protein in their oocytes and thereby allow for a recombination of sperm derived DNA after fusion of the nuclei (Hafner et al. (2004) Genesis 38: 176). Thus, all cells of resulting mice carry the recombined transgene. Offspring were tested positive for recombination based excision of the STOP sequence by PCR on the genomic level (iSE-mK14-H2Kk-Ml). Positive mice were again backcrossed to wt mice and offspring tested for expression of H2Kk by RT-PCR, Western Blot and FACS.

The male K14-Cre (mK14) expresses the Cre-gene specifically only in keratinocytes of the epidermis, hair follicles and the epithelium of the tongue. Offspring were tested for recombination based excision of the STOP sequence by PCR on the genomic level using tails biopsies which consists partly of keratinocytes (iSE-mK14-H2Kk-Ml). Liver tissue was used as a control and displayed no recombination event. Positive tested iSE-fK14-H2Kk-Ml were again tested for tissue specific expression of H2Kk by RT-PCR, Western Blot and FACS. For example, wild type, iSE-STOP-H2Kk-Ml, iSE-mK14-H2Kk-Ml, and iSE-fK14-H2Kk-Ml were tested for H2Kk expression in the Blood. Therefore, mice were anesthetized with KetamineHCl/Xylazine (0.08 mg/0.012 mg per g body weight, Sigma #K113) and sacrificed by cardial blood aspiration. Blood clotting was prevented by the addition of 14 µl EDTA (0.5 mol/l, Sigma #E6755) per 1 ml blood. Red blood cells were eliminated by incubation of 1 volume blood with 9 volumes of red cell lysis buffer (155 mmol/l NH4Cl, 10 mmol/l KHCO3 10 mmol/l EDTA, pH 7.4) for 1-3 min at room temperature until the milky red/turbid cell suspension was cleared. The remaining cells were pelleted by centrifugation with 200×g for 5 min and resuspended in PBS (Invitrogen #14190-169) in the initial blood volume (Invitrogen #14190-169).

The white blood cell suspension was first incubated on ice with mouse FCR blocking reagent (Miltenyi Biotec #130-092-575) 1:10 for 10 min and afterwards with the respective fluorescently conjugated antibodies mouse H2Kk-FITC (Miltenyi Biotec #130-085-101), mouse CD45-APC (Miltenyi Biotec #130-091-811), and mouse IgG2a-FITC (Miltenyi Biotec #130-091-837) each 1:11 in a final volume of 100 µl of PBS for 15 min. The incubation was stopped by adding 10 volumes of PBS and centrifugation with 200×g for 5 min. The cell pellet was resuspended in PBS and used for FACS analysis with a FACSCalibur flow cytometer (Beckton Dickinson) in a 1:1000 dilution with respect to the initial cell suspension. Dead cells were excluded from analysis by positive propidium iodide staining and according to scatter properties.

Figure 8:
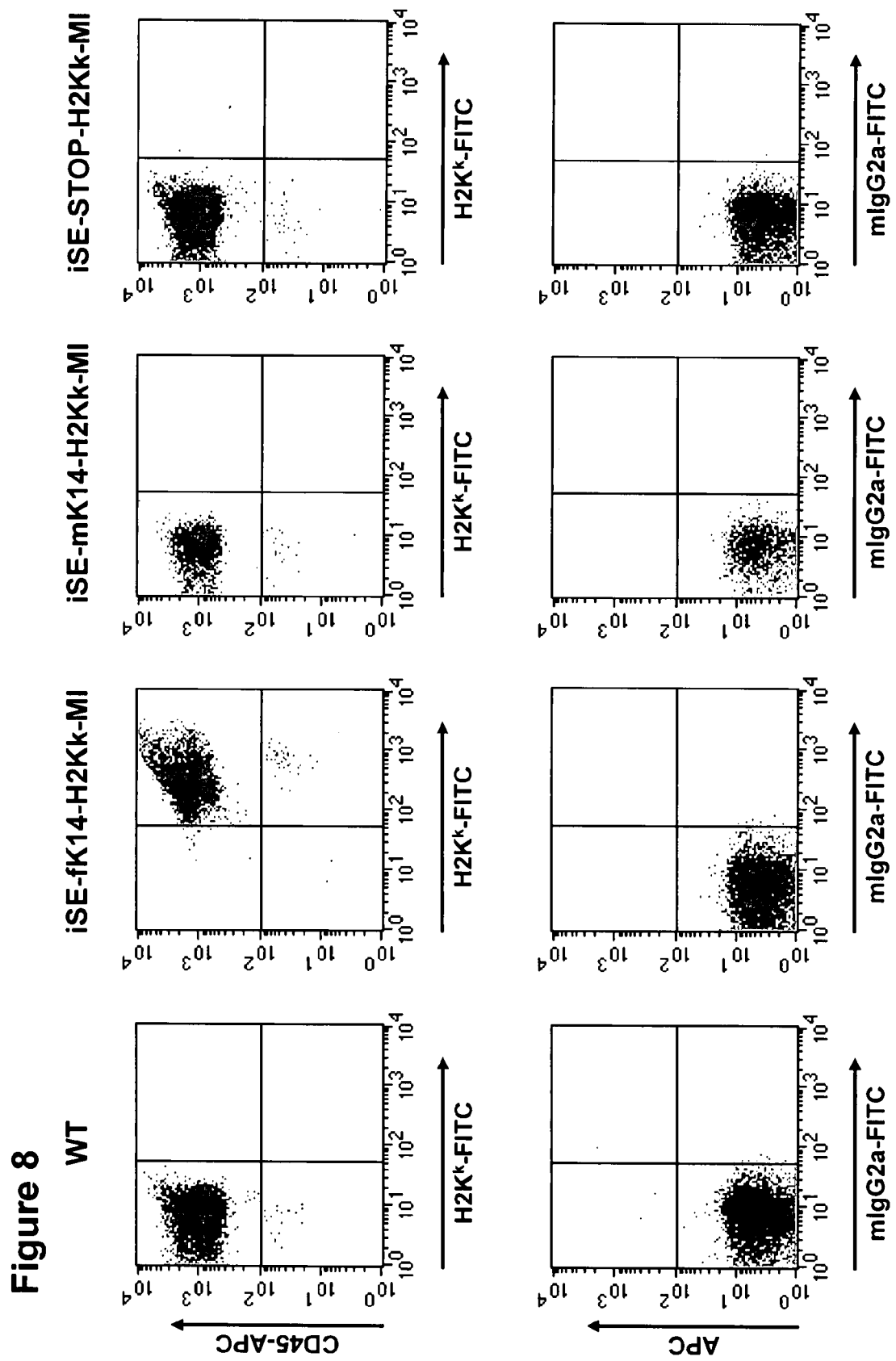
FIG. 8: shows the flow cytometric analysis comparing H2Kk transgene expression in the white blood cell population of four different mouse lines, wild type, iSE-STOP-H2Kk-Ml, iSE-mK14-H2Kk-Ml, and iSE-fK14-H2Kk-Ml. The lower panel shows the isotype control with mIgG2a-FITC antibody staining. The white blood cell population was further characterized by CD45-APC antibody staining in the upper panel.

FIG. 8 shows the flow cytometric analysis comparing H2Kk transgene expression in the white blood cell population of four different mouse lines. Lower panel shows the isotype control with mIgG2a-FITC antibody staining in the lower panel. The white blood cell population was further characterized by CD45-APC antibody staining in the upper panel. The wild type mouse (WT) shows no H2Kk expression in the white blood cell population whereas the ubiquitiously H2Kk expressing mouse (iSE-fK14-H2Kk-Ml) shows H2Kk expression in the whole white blood cell population. The keratinocyte specific H2Kk expressing mouse ((iSE-mK14-H2Kk-Ml H2Kk/K14-Cre) and the heterozygous H2Kk mouse ((iSE-STOP-H2Kk-Ml) without Cre-mediated elimination of the Westphal-STOP sequence show no H2Kk expression in the white blood cell population indicating a tight H2Kk expression block of the ROSA26-CAGG-STOP-H2Kk module. This example proves the in vivo expression of the inducible surface epitope.

To further analyze whether the transgenic expression of the H2Kk epitope has an influence on the distribution of cell types, the percentage of different immune cells in the spleen of iSE-fK14-H2Kk-Ml and wild type mice was determined. To this end, tissue was isolated, washed in HBSS (containing 10 mmol/l HEPES), and cut into small pieces using a scalpel. Chopped tissue was transferred to a 15 ml Falcon tube containing 2 ml HBSS. After adding Collagenase (Collagenase D: 2 mg/ml (referring to the Miltenyi Protocol: "Preparation of single-cell suspensions from mouse liver with Collagenase treatment"), Collagenase II, Worthington: 240 U/ml) and DNase (350 U/ml), the tube was incubated at 37° C. for 30 min and inverted several times during the incubation time. Tissue was completely dissociated by pressing it through a cells strainer (70 µm) using a sterile syringe plunger. The strainers were washed twice with 4 ml HBSS and the cell suspension was centrifuged at 1300 rpm for 5 min. Supernatant was discarded and the cell pellet was resuspended in an appropriate volume of flow cytometry buffer. Single-cell suspensions were labeled with anti H2Kk-PE conjugated antibody (clone: H100-27.R55) and the respective antibody directed against a blood cell marker for 10 min at 4° C. and analyzed by flow cytometry. Cell debris, erythrocytes and dead cells (identified by propidium-iodide) were excluded from the analysis. Data were acquired on a FACS-Calibur (BD-Bioscience).

TABLE 1

Analysis of H$_2$K$^k$ expression in different subpopulations of iSE-fK14-H2Kk-M1 spleen

| Blood cell marker | iSE-fK14-H$_2$K$^k$- Mouse: Percentage of cells double positive for H$_2$K$^k$ + respective blood cell marker | wild type: Percentage of cells double positive for H$_2$K$^k$ + respective blood cell marker | wild type: Percentage of cells positive for respective blood cell marker |
|---|---|---|---|
| CD45 (leukocytes) | 58.5 | 5.8 | 59.3 |
| CD3ε (T-cells) | 20.66 | 0.76 | 17.2 |
| CD25 (Tregs, activated T and B cells) | 1.75 | 0.07 | 1.77 |
| CD25 + CD4 (Tregs) | 0.7 | 0.07 | 0.4 |
| CD11c (dendritic cells) | 4.1 | 0.23 | 2.93 |
| CD19 (B-cells) | 33.4 | 1.65 | 39.7 |
| CD11b (mono-cytes/macrophages) | 6.5 | 0.64 | 5.8 |
| CD8a (cytotoxic T-cells) | 11.3 | 0.2 | 9 |
| CD49b (NK-cells) | 3.3 | 0.2 | 3.2 |

The analysis revealed that all CD45 positive cells do express the surface marker H2Kk. Furthermore, all cells of specific blood subpopulations, identified by a specific marker, were also detected by the anti H2Kk-antibody. As control, blood cells of a wild type mouse were stained and it was shown that the different blood cell subsets were not recognized by the anti H2Kk-antibody. However, the percentage of wilde type cells, which show expression of the respective blood cell marker, is similar to the percentage of transgenic cells double positive for H2Kk and respective blood cell marker (Table 1). This shows that the transgenic H2Kk expression is not toxic and has no deleterious effects.

The feasibility of magnetic cell sorting of transgenic H2Kk expressing cells was tested by sorting H2Kk positive keratinocytes from dissociated skin-tissue of iSE-mK14-H2Kk-M1. Skin biopsies were obtained from P2-P3 mice. Skin was placed in a PBS containing Petri dish and cut into small pieces. Tissue was then transferred to a 50 ml Falcon tube containing DMEM without FBS, 0.25% Trypsin and DNase (350 U/ml). After incubation at 37° C. for 1 h, the enzyme reaction was stopped by adding an equal amount of DMEM-Medium containing 10% FBS. The suspension was vortexed for 10 s and then applied to a 100 μm filter. Tissue was chopped by pressing it through the cell strainer using a sterile syringe plunger.

The Filter was rinsed thoroughly with DMEM (+10% FBS) and centrifuged at 300×g for 10 min. The cell pellet was resuspended in an appropriate amount of flow cytometry buffer and cell number was determined by using the Neubauer counting chamber.

Figure 9:
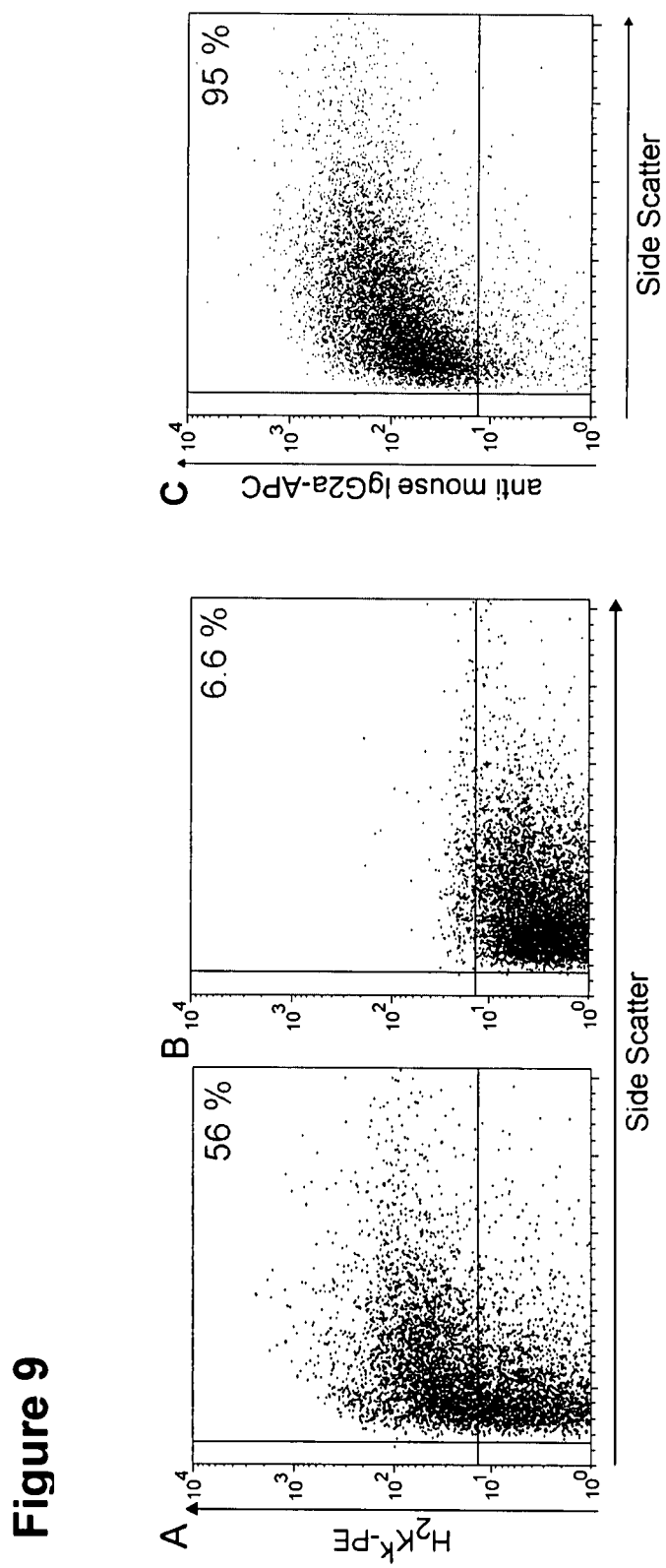
FIG. 9: shows the results of flow cytometric analysis, in which the percentage of H2Kk positive cells in the skin of iSE-mK14-H2Kk-Ml and iSE-STOP-H$_2$K$^k$ mice was determined.

As shown in FIGS. 9A and 9B, flow cytometric analysis of dissociated skin tissue obtained from iSE-mK14-H$_2$K$^k$-mice (9A) and iSE-STOP-H$_2$K$^k$-mice (9B) labeled with anti H$_2$K$^k$-PE antibody revealed that 56% of iSE-mK14-H$_2$K$^k$-mice express H2Kk. The H2Kk positive cells are supposed to be keratinocytes. Then, skin tissue of iSE-K14-H2Kk-mice was dissociated and H2Kk positive cells isolated by labeling with anti H2Kk MicroBeads and subsequent MACS. After the separation, the cells were stained with an antibody directed against the H2Kk MicroBeads (anti-mouse IgG2a-APC antibody). FIG. 9C shows that cells were sorted to a purity of 95%.

The invention claimed is:

1. A cultured mammalian cell containing a gene encoding a conditionally expressed transgenic extracellular surface marker that is detectable on the surface of the cell and exhibits one or both of resistance to digestion with trypsin and non-internalization by the cell upon binding of an antibody, wherein the gene encoding a conditionally expressed transgenic surface marker comprises:
   (i) a promoter for driving the transcription of a first transcription sequence, operably linked to
   (ii) a said first transcription sequence for preventing transcription of a second transcription sequence, thereby avoiding an immune response against the cell, wherein the first transcription sequence is conditionally removable by a CRE recombinase or a FLP recombinase, and
   (iii) a said second transcription sequence encoding the extracellular surface marker, comprising
      (a) a transmembrane or membrane association domain that anchors the surface marker in the cell membrane wherein at least a portion of the surface marker is on the extracellular side of the cell membrane, and
      (b) a tag sequence for rendering a cell sortable,
   whereby the first transcription sequence is conditionally removable such that the second transcription sequence is transcribable, and
   whereby the surface marker renders the cell sortable through the detection of the conditionally expressed transgenic surface marker on the extracellular surface of the cell.

2. The cell according to claim 1, wherein the conditionally expressed transgenic extracellular surface marker is expressed ectopically as a modified form of an endogenously expressed protein, whereby the modified form of endogenously expressed protein does not fulfill the same function as the endogenously expressed protein.

3. The cell according to claim 1, wherein the first transcription sequence is flanked on either side by a recombinase recognition site for conditional removal of the first transcription sequence from the gene, wherein the recombinase recognition sites flanking the first transcription sequence are the same.

4. The cell according to claim 1, wherein the second transcription sequence is a gene from the group consisting of LNGFR, H2Kk, CD133, CD271, CD2, CD14, CD90, or CD45 in an unmodified or modified form.

5. The cell according to claim 1, wherein the promoter is
a heterologous promoter,
a ubiquitous or tissue specific promoter, and/or
a constitutive or inducible promoter.

6. The cell according to claim 1, wherein the promoter is a promoter of a gene from the group containing: actin, CAGGS, hCMV, PGK, FABP, Lck, CamKII, CD19, Keratin, Albumin, aP2, Insulin, MCK, MyHC, WAP, Col2A, Mx, tet, Trex, and ROSA26.

7. An isolated mammalian cell containing a gene encoding a conditionally expressed transgenic extracellular surface marker that is detectable on the surface of the cell and exhibits one or both of resistance to digestion with trypsin and non-internalization by the cell upon binding of an antibody, wherein the gene encoding a conditionally expressed transgenic surface marker comprises:
   (i) a promoter for driving the transcription of a first transcription sequence, operably linked to
   (ii) a said first transcription sequence for preventing transcription of a second transcription sequence, thereby avoiding an immune response against the cell, wherein the first transcription sequence is conditionally removable by a CRE recombinase or a FLP recombinase, and
   (iii) a said second transcription sequence encoding the conditionally expressed extracellular surface marker, comprising
      (a) a transmembrane or membrane association domain that anchors the surface marker in the cell membrane wherein at least a portion of the surface marker is on the extracellular side of the cell membrane, and
      (b) a tag sequence for rendering a cell sortable,
   whereby the first transcription sequence is conditionally removable such that the second transcription sequence is transcribable, and
   whereby the surface marker renders the cell sortable through the detection of the conditionally expressed transgenic surface marker on the surface of the cell.

* * * * *